US009671400B2

(12) United States Patent
Lohse

(10) Patent No.: US 9,671,400 B2
(45) Date of Patent: *Jun. 6, 2017

(54) CONJUGATE MOLECULES

(75) Inventor: Jesper Lohse, Herlev (DK)

(73) Assignee: Dako Denmark A/S, Glostrup (DK)

( * ) Notice: Subject to any disclaimer, the term of this patent is extended or adjusted under 35 U.S.C. 154(b) by 1591 days.

This patent is subject to a terminal disclaimer.

(21) Appl. No.: 12/708,702

(22) Filed: Feb. 19, 2010

(65) Prior Publication Data
US 2010/0240085 A1 Sep. 23, 2010

Related U.S. Application Data

(60) Provisional application No. 61/153,699, filed on Feb. 19, 2009, provisional application No. 61/253,116, filed on Oct. 20, 2009.

(51) Int. Cl.
C12Q 1/28 (2006.01)
G01N 33/543 (2006.01)
C08G 63/672 (2006.01)
C08G 69/40 (2006.01)
C08G 69/48 (2006.01)

(52) U.S. Cl.
CPC ..... G01N 33/54393 (2013.01); C08G 63/672 (2013.01); C08G 69/40 (2013.01); C08G 69/48 (2013.01); C12Q 1/28 (2013.01)

(58) Field of Classification Search
CPC ...... C08G 63/672; C08G 69/40; C08G 69/48; C12Q 1/28; G01N 33/5493; G01N 33/54306; G01N 33/581
See application file for complete search history.

(56) References Cited

U.S. PATENT DOCUMENTS

| 5,196,306 | A | 3/1993 | Bobrow et al. |
| 5,583,001 | A | 12/1996 | Bobrow et al. |
| 5,585,089 | A | 12/1996 | Queen et al. |
| 5,688,966 | A | 11/1997 | Bobrow et al. |
| 5,731,158 | A | 3/1998 | Bobrow et al. |
| 5,767,287 | A | 6/1998 | Bobrow et al. |
| 5,863,748 | A | 1/1999 | Bobrow |
| 6,372,937 | B1 | 4/2002 | Bobrow et al. |
| 6,517,739 | B2 * | 2/2003 | Sugino et al. ........... 252/299.66 |
| 6,593,100 | B2 | 7/2003 | Bobrow et al. |
| 2008/0305497 | A1 | 12/2008 | Kosmeder et al. |
| 2009/0215646 | A1* | 8/2009 | Anslyn et al. ................. 506/12 |
| 2010/0285467 | A1 | 11/2010 | Lohse et al. |

FOREIGN PATENT DOCUMENTS

| CN | 1402005 A | 3/2003 |
| EP | 0 436 597 B1 | 4/1997 |
| EP | 0 623 679 B1 | 6/2003 |
| EP | 0 368 684 B2 | 9/2004 |
| EP | 0 589 877 B2 | 10/2005 |
| WO | WO 2007/015168 | * 2/2007 |
| WO | WO 2007/015168 A2 | 2/2007 |
| WO | WO 2009/036760 A2 | 3/2009 |
| WO | WO 2010/094284 A1 | 8/2010 |

OTHER PUBLICATIONS

Lewandowski et al. (Tyrosine-based "activatable pro-tag": enzyme-catalyzed protein capture and release, 2006, Biotechnology and Bioengineering, vol. 93, pp. 1207-1215).*
Chemical Book (http://www.chemicalbook.com/ChemicalProductProperty_EN_CB9412697.htm accessed on Dec. 3, 2012, 1 page).*
Kohler, G. et al., "Continuous Cultures of Fused Cells Secreting Antibody of Predefined Specificty", Nature, 256:495-497, (1975).
McCafferty, J., et al., "Phage Antibodies: Filamentous Phage Displaying Antibody Variable Domains", Nature, 348:552-554, (1990).
Kang, A., et al., "Linkage of recognition and replication functions by assembling combinatorial antibody Fab libraries along phage surfaces", Proc. Natl. Acad. Sci., 88:4363-4366, (1991).
Marks, J., et al., "By-Passing Immunization: Building High Affinity Human Antibodies by Chain Shuffling", Bio/Tech., 10:779-783, (1992).
Waterhouse, P. et al., "Combinatorial Infection and In Vivo Recombination: A Strategy for Making Large Phage Antibody Repertoires", Nucleic Acids Reas. 21(9):2265-2266, (1993).
Jones, R. "Cancer Risk Assessments in Light of Chernobyl", Nature, 323:585-586, (1986).
Nielsen, P. "Peptide Nucleic Acid: A Versatile Tool in Genetic Diagnostics and Molecular Biology".
Sørensen, M., et al., "Functionalized LNA (locked nucleic acid): High-Affinity Hybridization of Oligonucleotides Containing N-Acylated and N-Alkylated 2'-Amino-LNA Monomers", Chem. Commun., 2130-2131, (2003).
Altschul, S., et al., "Gapped BLAST and PSI-BLAST: A New Generation of Protein Database Search Programs", Nucleic Acids Res., 25(17):3389-3402, (1997).
Good, N. et al., "Hydrogen Ion Buffers for Biological Research", Biochemistry, 5(2):467-477, (1966).
Shi, S. R. et al., "Antigen Retrieval Immunohistochemistry: Past, Present and Future", J. Histochem. & Cytochem., 45(3):327-343, (1997).
Volante, M., et al., "Post-Incubation heating Significantly Improves Tyramide Signal Amplification", J. Histochem. & Cytochem., 48(11):1583-1585, (2000).
Bobrow, M. et al., "Catalyzed Reporter Deposition, A Novel Method of Signal Amplification", J. Immuno. Meth., 125:279-285, (1989).
Bobrow, M. et al., "The Use of Catalyzed Reporter Deposition as a Means of Signal Amplification in a Variety of Formats", J. Immuno. Meth., 150:145-149, (1992).
U.S. Appl. No. 12/708,710, filed Feb. 19, 2010.
Takei, K., et al., "Regulation of Enzyme-Substrate Complexation by a Substrate Conjugated with a Phospholipid Polymer", Biomacromolecules, pp. 858-862, 2004.

* cited by examiner

Primary Examiner — Susan Hanley

(57) ABSTRACT

The present invention relates to compounds which are conjugates of two or more moieties capable of serving as substrates of an enzyme with peroxidase activity and one or more labels. The conjugate molecules of the invention are useful for detection of molecular targets, e.g. biological or chemical molecules, molecular structures, etc, in samples using a host of experimental schemes for detecting and visualizing such targets, e.g. immunohistochemistry (IHC), in situ hybridization (ISH), ELISA, Southern, Northern, and Western blotting, etc. The invention also relates to compositions comprising the conjugate molecules.

24 Claims, 3 Drawing Sheets

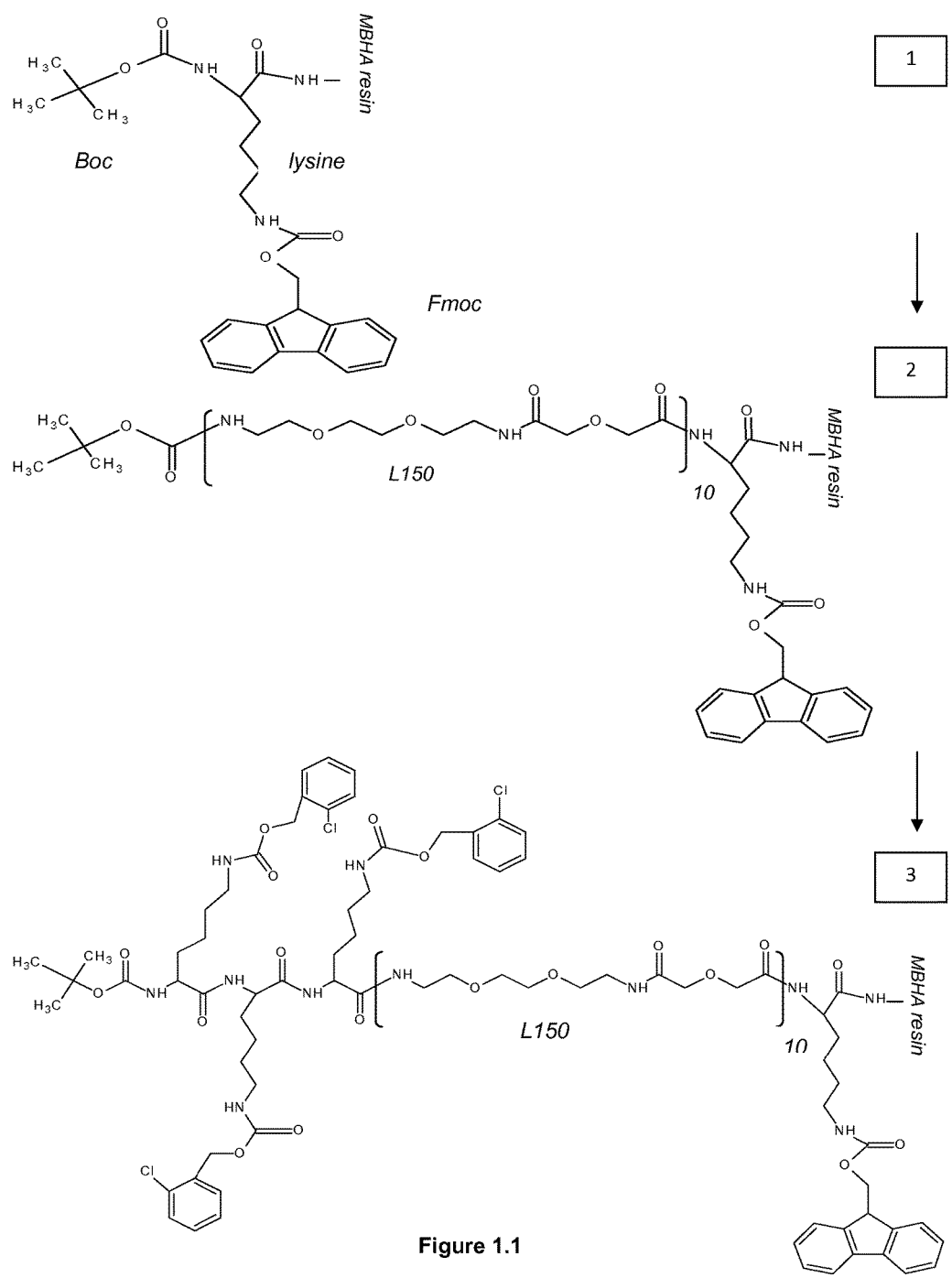
Figure 1.1

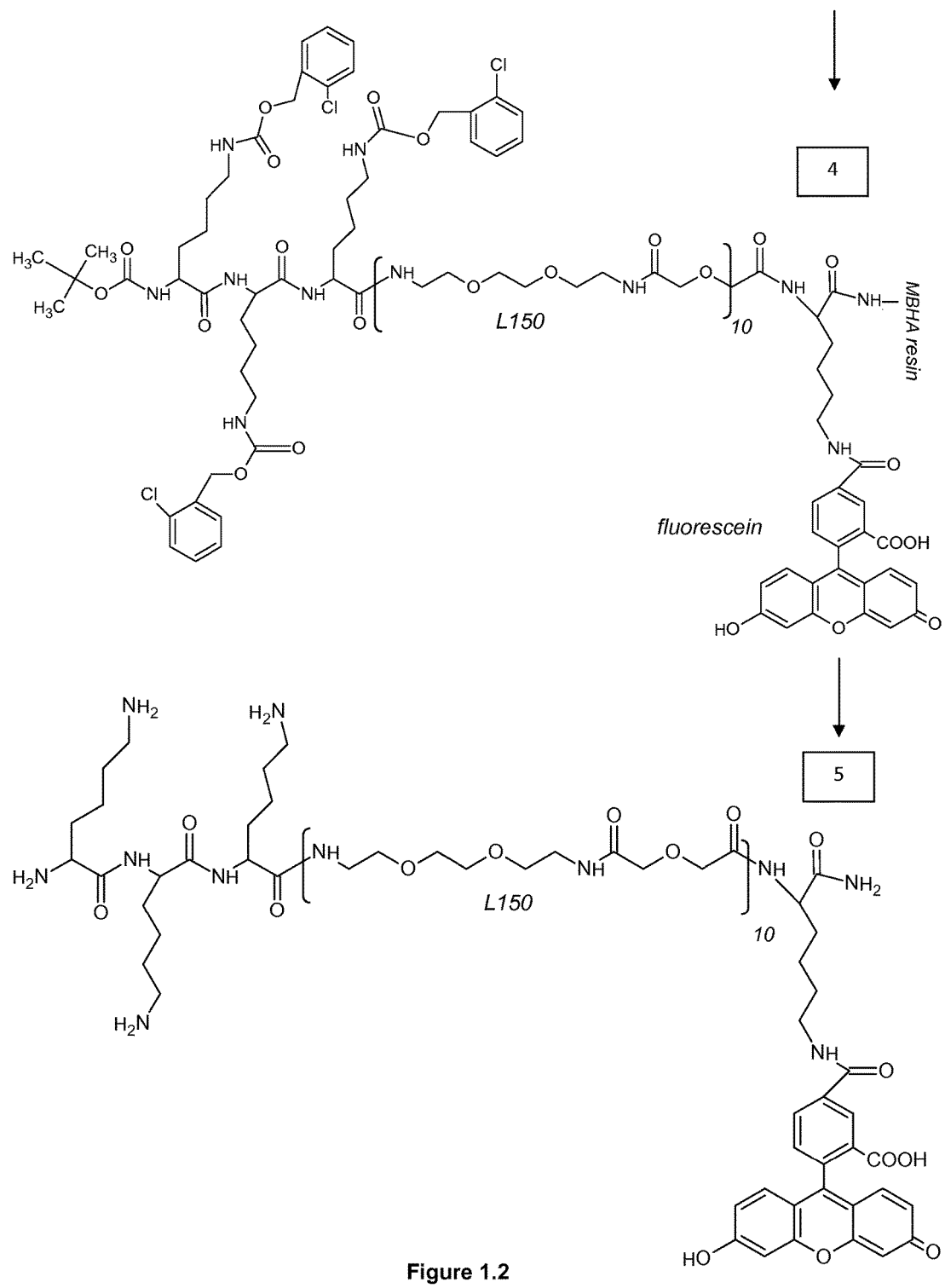
Figure 1.2

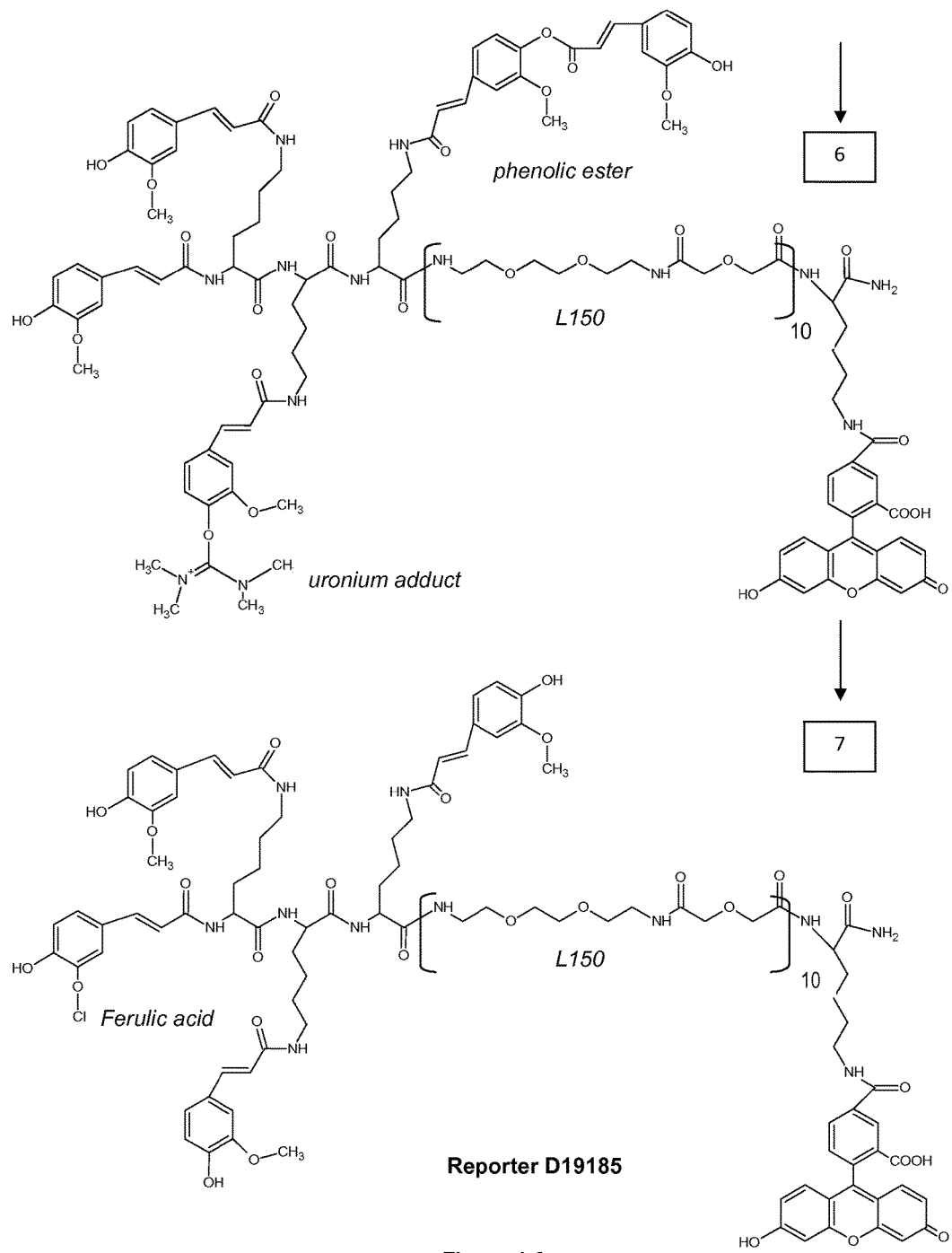
Figure 1.3.

CONJUGATE MOLECULES

This application claims the benefit of provisional application No. 61/153,699, filed on Feb. 19, 2009, and provisional application No. 61/253,116, filed on Oct. 20, 2009. The entire disclosures of the prior applications are relied upon and incorporated herein by reference.

FIELD OF THE INVENTION

The present invention relates to compounds which are conjugates of two or more moieties capable of serving as substrates of an enzyme with peorxidase activity and one or more labels. The conjugate molecules of the invention are useful for detection of molecular targets, e.g. biological or chemical molecules, molecular structures, etc, in samples using a host of experimental schemes for detecting and visualizing such targets, e.g. immunohistochemistry (IHC), in situ hybridization (ISH), ELISA, Southern, Northern, and Western blotting, etc. The invention also relates to compositions comprising the conjugate molecules.

BACKGROUND

Detection of a biological or chemical target in a sample using a detectable label is a procedure at the heart of many biological detection methods, including medical diagnostic methods. In some cases the target may be a particular polynucleotide sequence or gene, a mutation of a gene, a genetic expression pattern, detected at the DNA or RNA level, either in situ or after extraction or isolation. In other cases, the target may be a peptide, protein, antigen, or other substance, again detected in situ or after isolation or laboratory manipulation. The target may also be a particle or debris of organic origin.

Many standard detection methods, e.g. IHC, ISH, ELISA, blotting, etc., employ labeling schemes to detect the desired targets. Typically, those schemes involve incubating an experimental sample potentially containing the detectable target with a probe, and then detecting the binding between binding agent and target with a detectable label which may give off a color, a fluorescent signal, or radioactivity, for example. One or many binding agent molecules may bind to each target, depending upon the specifics of the scheme used. In some cases, especially when the target is present in low concentration, it is necessary to amplify the signal from the target-binding agent complex by adding one or more amplification layers to the system. For example, if the binding agent is a primary antibody that recognizes the target, a secondary antibody that recognizes the primary antibody may be added such that many secondary antibodies bind to each primary antibody. If the secondary antibodies are attached to a detectable label such as a fluorophore or chromophore, then, via amplification, each target molecule in the sample may effectively be bound to multiple fluorophores or chromophores instead of only one or a few fluorophores or chromophores. Hence, the target will produce a stronger detection signal after amplification.

Some detection experiments, however, have a tendency to produce relatively diffuse-looking signals, especially if the sample is allowed to rest for a period of time before analysis. For example, the one or more binding agents and/or detectable labels bound to a target may slowly diffuse away from the target, or away from each other over time. In some cases buffer changes that affect the binding affinity of the target, binding agent, and amplification layers can also cause signal diffusion. Many detectable labels are bound to targets by non-covalent interactions such as protein-ligand binding or polynucleotide hybridization. Buffer changes after labeling may reduce the affinity between the target, binding agent, and detectable label, causing the various components to dissociate. Simple diffusion over a period of time, such as several days, may also cause dissociation between target, binding agent, and detectable label, rendering the signal diffuse.

Other problem associated with currently available detection procedures, in particular immunodetection, is time consumption. It normally takes 1 to 3 hours at minimum to process a sample from the step of labeling of targets to detection of the label.

Prior art describes only a very few techniques which allow to overcome the above mentioned problems, but yet only partially. One example of such techniques is a method of catalyzed conjugate deposition (CARD) described in U.S. Pat. Nos. 5,863,748; 5,688,966; 5,767,287; 5,731,158; 5,583,001, 5,196,306, 6,372,937 or 6,593,100. This method utilizes so-called "analyte-dependent enzyme activation system" (ADEAS) to catalyze the deposition of a detectable label onto the solid phase of an assay platform. In the assay format, an enzyme comprised by the ADEAS reacts with a conjugate consisting of a detectably labeled substrate specific for the enzyme. When the enzyme and the conjugate react, an activated conjugate is formed which deposits covalently at a site where a specific receptor for the activated conjugate is immobilized. Thus, because of the conjugate comprises a label it plays a role of a conjugate which indicates the presence of a target in the site. Enzymatically deposited labels may be detected directly or indirectly. The method results in signal amplification and improved detection limits.

The CARD method may be used in assay formats, where the target to be detected is a receptor immobilized on a solid support, e.g. a membrane. Such assays formats include sandwich immunoassays and membrane based nucleic acid hybridization assays. The CARD method is also applicable to detection of biological targets e.g. by immunohystochemistry (IHC), as described in U.S. Pat. No. 6,593,100. The method described in U.S. Pat. No. 6,593,100 utilizes a reaction of horse radish peroxidase (HRP) with a labeled conjugate comprising a HRP substrate in the presence of an enhancer. Both HRP substrate and enhancer are derivatives of phenol. Upon reaction with HRP the HRP substrate becomes activated and binds to receptor sites of the sample which are typically represented by low abundance aromatic amino acid residues of proteins.

Despite of having a relatively good sensitivity of detection of target molecules in samples compared to many other currently available methods, in particular methods for immunohistochemical detection of targets, the CARD method does not fully solve the other method's problems, for example strong background staining, still insufficient sensitivity and time consumption, which burden the method in cases of histological samples improperly proceeded prior the staining or those having a low level of target expression.

Recently, it has been described another HRP-based amplification method allowing detection of low abundance target molecules in IHC samples (WO2009036760). The method utilizes DAB not as a chromogenic substrate of HRP, but as a cross-linking agent of other HRP substrates. According to WO2009036760 DAB mediates HRP-mediated deposition of other HRP substrates, itself being not deposited DAB, i.e. there is no is characteristic visible brownish deposits is formed under conditions of the described deposition. The deposits of the other HRP substrate are detectable because they comprise a detectable label associated with the HRP substrate molecule, e.g. they may be detected in steps following the deposition step. The method provides for a strong amplification of a signal of the deposited HRP substrate, which makes the sensitivity of the method to be comparable with the CSA method, but compared to the latter method the new method advantageously provides no background labeling. Among other advantages of this new method, it is worth to mention that the speed of the detection procedure is much faster than either traditional DAB or biotinyl-tyramide detection procedure.

SUMMARY OF INVENTION

The present invention relates to compounds and compositions that may advantageously improve detection of molecular targets, in particular molecular targets comprising peroxidase activity. In particular compounds and compositions of the invention improves detection by the method described in WO2009036760 in that a more quick, sensitive and precise detection of molecular targets is achieved.

In one aspect, the invention relate to a water soluble conjugate molecule comprising a water soluble polymer comprising a linear chain of at least 30 interconnected atoms, wherein said polymer is conjugated with at least one detectable label and at least two moieties capable of serving as substrate of a peroxidase enzyme, wherein the at least one detectable label and the at least two moieties are spaced from each other by a distance corresponding to a chain of at least 30 interconnected atoms, wherein a distance between any two moieties of the substrate of the peroxidase enzyme is less than a chain of 30 interconnected atoms.

In one aspect the invention relates to a water soluble conjugate molecule that comprises
(i) one or more detectable substances,
(ii) at least two substances, each thereof is capable of serving as substrate of an enzyme with peroxidase activity,
wherein the labels (i) and moieties of peroxidase substrate (ii) are not the same chemical substances;
wherein
the labels (i) and peroxidase substrates moieties (ii) are linked together via a linker, wherein said linker is a compound comprising at least one linear chain of at least 30 consecutively connected atoms, wherein said linear chain of atoms contain at least two branching points separated by a distance of at least 30 consecutively connected atoms;
wherein
the labels (i) and peroxidase substrate moieties (ii) are separated in the conjugate molecule by least 30 consecutively connected atoms, and
wherein
two neighboring of the peroxidase substrate moieties are separated from each other by less than 30 consecutively interconnected atoms.

In one embodiment, the moieties capable of serving as substrate of an enzyme with peroxidase activity has the following formula:

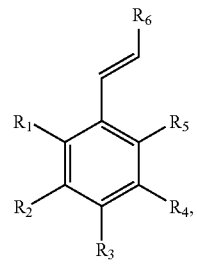

wherein
R1 is —H, —O—X, N(X)$_2$ or —S—X;
R2 is —H, —O—X, —N(X)$_2$, or —S—X,
R3 is —H, —OH, —NH$_2$ or —SH;
R4 is —H, —O—X, —N(X)$_2$, or —S—X,
R5 is —H, —O—X, N(X)$_2$, or —S—X,
R6 is —CON(X)$_2$, or CO—X,
wherein
H is hydrogen;
O is oxygen
S is sulphur
N is nitrogen, and
X is H, alkyl or aryl.

In one embodiment the moieties of peroxidase substrate are residues of ferulic acid cinnamic acid, amino cinnamic acid, caffeic acid, sinapinic acid, or tyrosine.

In one embodiment, at least two of the moieties that are capable of serving as substrate for a peroxidase enzyme are tyrosine residues.

In one embodiment, the one linear chain of at least 30 consecutively connected atoms of a conjugate molecule comprises 2 repeats of the following formula

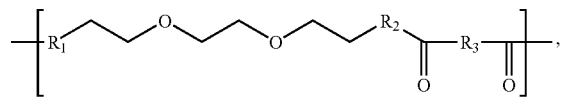

wherein $R_1$ and $R_2$ are selected from NH and O, and $R_3$ is selected from methyl, ethyl, propyl, CH$_2$OCH$_2$, and (CH$_2$OCH$_2$)$_2$, and wherein no more than three consecutively repeating ethyloxy groups.

In one embodiment, a conjugate molecule comprises 2-4 moieties capable of serving as substrate for a peroxidase enzyme and 1 detectable label wherein the labels and the moieties are liked to a linear polymer comprising 2 to 10 repeats of a compound of the above formula, which polymer has at least two branching points at the opposite ends of the polymer chain, wherein said moieties and said label are attached to the polymer at said opposite branching points.

In one embodiment, a conjugate molecule comprises a dextran polymer conjugated to at least one first and at least one second linear polymers, wherein said at least first polymer is conjugated to two to four moieties that are capable serving as peroxidase enzyme substrate, and said at least one second polymer is conjugated to one or more detectable labels. In one embodiment the second polymer comprises two or more labels, wherein a molecular distance between two neighboring labels is at least 30 consecutively connected atoms.

In one embodiment, the detectable label is a fluorescent substance or a member of a specific binding pair.

In one embodiment, the enzyme with peroxidase activity is horse radish peroxidase.

The invention also relates to compositions comprising conjugate molecules according to the invention and kits-of-parts for detection of targets or peroxidase activity in a sample.

Further, the invention in one aspect related to a method for detection of peroxidase activity in a sample, comprising I. incubating a sample supposedly peroxidase activity in a water solution comprising:
   a) a compound according to any of claims 1 to 10,
   b) 3,3' diaminobenzidine, and
   c) a peroxide compound,
   thereby forming a precipitate of the compound;
II. detecting the precipitate of the compound in the sample, thereby detecting peroxidase activity in the sample.

In one embodiment the method of invention is for detection a target in a sample, e.g. target molecule. In one embodiment, horse radish peroxidase is directly or indirectly linked to the target. In one embodiment, the sample is a biological sample, environmental sample, or chemical sample. In one embodiment, the sample or/and target is immobilized onto a solid suppot In one embodiment, the methods of the invention use a water solution of a conjugate molecule of the invention which comprises more than 5 mM hydrogen peroxide and between 0.25 mM and 6 mM 3,3' diaminobenzidine, or a solution wherein the amount of 3,3' diaminobenzidine is above 1.5 mM The conjugate compound of the invention in some embodiment is interchangeably termed "conjugate" or reporeter molecule".

DESCRIPTION OF DRAWINGS

FIG. 1, panels 1.1-1.3, is a schematic presentation of synthesis of an exemplary conjugate molecule of the invention (for details see EXAMPLES).

DETAILED DESCRIPTION OF INVENTION

Conjugate Molecules

The invention relates to a large group of conjugate molecules (interchangeably termed "conjugates") that share the following features:

1. The conjugate molecules are water soluble molecules comprising two or more substances that can serve as substrate of a peroxidase enzyme, preferably HRP substrates and one or more labels which are linked together via a water soluble liker compound;
2. The peroxidase substrate moieties are "concentrated" in the conjugate molecule in one part of said molecule in that they are separated from each other by a distance of not more than 2.5 nm, e.g. separated within molecule of the conjugate by less than 30 interconnected carbon atoms or heretoatoms, such as carbon, nitrogen, sulphur and/or oxygen, preferably by more than 5-20 atoms chain;
3. The detectable label(s) are distanced away from the peroxidase substrate moieties by at least 30 consecutively interconnected atoms, i.e. distanced away by more than 2.5 nm, preferably more than 3 nm;
4. The linker preferably comprises a polymer comprising at least one linear chain at least 30 consecutively connected atoms; preferably, wherein two consecutive carbons followed by an oxygen or nitrogen atom;
5. The conjugates do not precipitate from water solutions containing a peroxide compound and 3,3'-diaminobenzedine (DAB) in the absence of an enzyme having peroxidase activity in the environment.
6. The conjugates do not precipitate from water solutions containing a peroxide compound but not containing 3,3'-diaminobenzedine (DAB) in the presence of an enzyme having peroxidase activity in the environment
7. The conjugates precipitate from water solutions containing a peroxide compound and 3,3'-diaminobenzedine (DAB) in the presence of an enzyme having peroxidase activity in the environment These features are described in detail below and some conjugate molecules that have these features are exemplified in EXAMPLES.

In one aspect the invention relates to a water soluble conjugate molecule that comprises
   (i) one or more detectable substances (termed interchangebly "label")
   (ii) at least two substances, which are capable of serving as substrates of an ezyme with peroxidase activity (such substances are termed "peroxidase substrates" or "moieties of peroxidase substrate"),
      wherein the labels (i) and moieties of peroxidase substrate (ii) are not the same chemical substances,
      wherein
      the labels (i) and peroxidase substrates moieties (ii) are linked together via a linker, wherein said linker is a compound comprising at least one linear chain of at least 30 consecutively connected atoms, wherein said linear chain contain at least two branching points separated by a distance of at least 30 consecutively connected atoms;
      wherein
      the labels (i) and peroxidase substrate moieties (ii) are separated in the conjugate molecule by least 30 consecutively interconnected atoms, and
      wherein
      two neighboring of the peroxidase substrate moieties are separated from each other by less than 30 consecutively interconnected atoms The term "detectable substance" is relates to a substance that (i) can give off a detectable chromogenic, fluorescent, luminescent or radioactive signal, or (ii) is a member of a specific binding pair, e.g. an antibody, nucleic acid sequence, nucleic sequence analog sequence, hapten, antigen, receptor, receptor ligand, enzyme, etc. that thut signal can be detected.

In some embodiments a water soluble conjugate molecule of the invention may additionally comprise moieties that may enhance their features, i.e. as label and/or peroxidase substrate moiety, or increase/reduce water solubility of the molecule.

A conjugate molecule of the invention may be presented by the following formula (I):

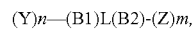

wherein
Y is a moiety capable of serving as substrate of an enzyme with peroxidase activity;
Z is a detectable label;
L is a linker
B1 and B2 are brunching points,
wherein
n is an integer from 2 to 150, and
m is an integer from 1 to 150

In one preferred embodiment Y has the following formula (II):

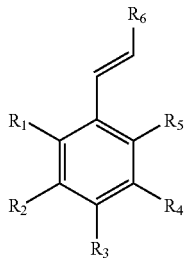

wherein
R1 is —H, —O—X, N(X)₂ or —S—X;
R2 is —H, —O—X, —N(X)₂, or —S—X,
R3 is —H, —OH, —NH₂ or —SH;
R4 is —H, —O—X, —N(X)₂, or —S—X,
R5 is —H, —O—X, N(X)₂, or —S—X,
R6 is —CON(X)₂, or CO—X,
wherein
  H is hydrogen;
  O is oxygen
  S is sulphur
  N is nitrogen, and
  X is H, alkyl or aryl.

In one preferred embodiment Y is a residue of cinnamic acid; in another preferred embodiment Y is a residue of ferulic acid. In another preferred embodiment Y is a residue of caffeic acid; in another preferred embodiment Y is a residue of amino cinnamic acid. In another preferred embodiment Y is a residue of sinapinic acid. In another preferred embodiment, Y is a derivative of ferulic acid, cinnamic acid, caffeic acid, amino cinnamic acid or sinappinic acid.

Preferably a residue Y of the formula (II) is connected to L via group R6.

In one preferred embodiment the conjugate may comprise two to four identical or different residues Y.

In one preferred embodiment a conjugate molecule may comprise two Y molecules of formula (II), e.g. two ferulic acid residues, or two cinnamic acid residues, or two amino cinnamic acid residues, or two caffeic acid residues, or two sinapinicacid residues, and one or more detectable labels; in another embodiment the conjugate may comprise three molecules of formula (II), e.g. tree ferulic acid, cinnamic acid, caffeic acid, amino cinnamic acid or sinapinic acid residues, and one or more detectable label; in another embodiment the conjugate may comprise three or four molecules of formula (II), e.g. four ferulic acid, cinnamic acid, caffeic acid, amino cinnamic acid or sinapinic acid residues, and one or more detectable labels.

In some embodiments the number of Y residues may be higher than 4, e.g. such as 5-10, 10-15, 15-20, 20-50, 50-100, or 100-150 molecules. Non-limiting working examples of such conjugate molecules are described in Examples. Preferably, such conjugates comprise more than one linear chain of at least 30 consecutively connected atoms, e.g. 30-150 atoms, wherein two to four Y residues are linked to each linear chain at first branching point of the chain (in a mode described below), and several of such linear chains are linked to another water soluble polymer, e.g. a dextran, via a second branching point of their chains.

In one preferred embodiment, a conjugate molecule may comprise two or more different molecules of formula (II).

In one preferred embodiment Y may be a residue of amino acid tyrosine or a derivative thereof. A conjugate may comprise 2 to 4 tyrosine residues, or more tyrosine residues.

According to the invention, two to four Y residues are preferably located in a conjugate molecule as a group (i.e. a conjugate comprising more than four more than four Y residues comprises several groups of two to four Y residues separated in the conjugate molecule by some distance, e.g. 30 connected atoms or more). Preferably, the two to four Y residues are linked together via a compound (spacer) that provides a distance between two neighboring Y residues which is not longer than 5-30 interconnected atoms, e.g. 5-10, 6-12, 7-13, 8-14, 9-15, 10-16, 11-17, 12-18, 13-19, 20, 21, 22, 23, etc. For example, 2-4 Y residues may be linked to a peptide chain comprising 2 to 4 amino acid, e.g. lysine residues, wherein the Y residues are attached to side chain reactive groups of the amino acid residues of the peptide, e.g. epsilon amino acid residues of lysine residues. Two to four may be connected via other short polymers which comprise a number of brunching points with the distance between these branching points of not more than 3-5 atoms, preferably 3 atoms, wherein the Y residues may be linked to side chains of atoms or chemical groups of these polymers. Such grouped location of Y residues is termed herein "Y-head" of the conjugate molecule.

In one preferred embodiment, the Y-head comprises two to four Y-residues linked via a short polymer, e.g. a PNA or a peptide, wherein the peptide preferably comprises lysine, serine glutamate or cystein residues. However, any other short polymer that can be conjugated with at least two Y-residues and a linker L may be suitable.

In one embodiment an Y-head comprising two to four residues Y is linked to a polymer comprising two or more residues of a molecule of the following formula (III)

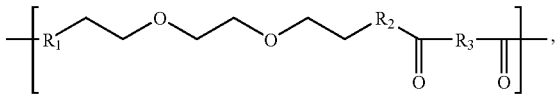

wherein R₁ and R₂ are selected from NH and O, and R₃ is selected from methyl, ethyl, propyl, CH₂OCH₂, and (CH₂OCH₂)₂, and wherein no more than three consecutively repeating ethyloxy groups. The resulting conjugate may be than further conjugated with one detectable label (or more than one detectable label as described below), or it may be conjugated with a water soluble polymer (which can be linked with one or several such conjugates), e.g. dextran.

Close spacing of Y residues in the conjugate molecules of the invention influence the features of conjugates (compared to conjugates that comprise the only Y residue or comprise several Y residues that are not "concentrated" in the conjugate molecule in form of an Y-head, i.e. molecular space between two neighboring Y residues is larger than the discussed above distance) in that the conjugates are soluble in water solutions containing a peroxide compound and 3,3'-diaminobenzedine (DAB) in the absence of an enzyme having peroxidase activity in the environment, but quickly and abundantly precipitate from such solutions in the presence of an enzyme having peroxidase activity in the environment The detectable label, Z, may be any substance which can be visually detected, e.g. a fluorescent or luminescent substance, or any substance that can be detected by using some detecting means, e.g. a radioactive label, a member of a specific binding pair, e.g. a nucleic acid sequence, hapten, etc.

Any fluorescent, luminescent, bioluminescent or radioactive molecules may be used as the labels. Many of them are commercially available, for example fluorescent stains Alexa Fluors (Molecular Probes) and DyLight Fluors (Thermo Fisher Scientific). Other non-limited examples of fluorescent labels may be the following molecules: 5-(and 6)-carboxyfluorescein, 5- or 6-carboxyfluorescein, 6-(fluorescein)-5-(and 6)-carboxamido hexanoic acid, fluorescein isothiocyanate, rhodamine, tetramethylrhodamine, Cy2, Cy3, Cy5, AMCA, PerCP, R-phycoerythrin (RPE) allophycoerythrin (APC), Texas Red, Princeton Red, Green fluorescent protein (GFP) coated CdSe nanocrystallites, ruthenium derivatives, luminol, isoluminol, acridinium esters, 1,2-dioxetanes and pyridopyridazines, radioactive isotopes of hydrogen, carbon, sulfur, iodide, cobalt, selenium, tritium, or phosphor.

In some embodiments the detectable label may be an enzyme. Non-limiting examples of suitable enzyme labels may be alkaline phosphatase (AP), beta-galactosidase (GAL), glucose-6-phosphate dehydrogenase, beta-N-acetyl-glucosaminidase, β-glucuronidase, invertase, xanthine oxidase, firefly luciferase, glucose oxidase (GO).

In other embodiments, the detectable label may be a member of a specific binding pair, e.g. a hapten. As non-limiting examples of suitable haptens may be mentioned 2,4-dinitrophenol (DNP), digoxigenin, fluorescein, Texas Red, tetra methyl rhodamine, nitrotyrosine, acetylaminoflurene, mercury trintrophonol, estradiol, bromodeoxy uridine, dimethylaminonaphthalene sulfonate (dansyl); as examples of suitable specific binding pairs may be mentioned biotin, streptavidin, complementary natural and non-natural oligonucleotide sequences, zink fingers binding domain pairs, etc. Other examples of members of specific binding pairs are discussed in above sections.

In one preferred embodiment the label is a hapten. In another preferred embodiment, the label is a fluorescent substance. In another preferred embodiment, the label is a member of a specific binding pair.

The number or detectable labels per conjugate molecule may vary. In some embodiments 1 to 3, for example 1, 2 or 3 labels per conjugate molecules may be preferred. In a preferred embodiment such conjugate comprises one detectable label. In one embodiment a conjugate molecule comprising two to four residues Y of the formula (II) or two to four tyrosine and one single label may be preferred. In some embodiments, the conjugate may comprise more than 3 labels, such as 4 to 150 labels per conjugate molecule.

According to the invention, in a conjugate molecule the label(s) are separated from the peroxidase substrate moieties, e.g. from an Y-head, by a distance of more than 2.5 nm, e.g. separated by a chain of at least 30 consecutive atoms, e.g. 60, 90 or 150 consecutive atoms. In embodiments where the conjugate comprises one linear chain of atoms linking a Y-head and 1 (or more) labels, the Y-head and the label(s) are linked to said chain at branching points located on the opposite ends of the chain.

In some embodiments, when a conjugate comprises more than 1 label, it is preferred that the labels are conjugated to the linker (i.e. to a substance linking labels and peroxidase moieties in one molecule) so that there is a distance between sites of attachment of the labels, which distance correspond to a chain of at least 30 consecutively connected atoms (termed "spacing moiety" or "spacer"), preferably 60 consecutively atoms or more, e.g. 90 consecutively interconnected atoms. It is preferred that the spacing moiety between the attached labels is hydrophilic. Such arrangement of multiple labels in a conjugate molecule is termed herein "Z-tail". It is understood, that a label of a Z-tail comprising multiple labels which is positioned closest to a Y-head is distanced away from any of the peroxidase moieties of the Y-head by at least 30 interconnected atoms, i.e. by at least 2.5 nm distance.

Preferably, the spacer of at least 30 consecutive atoms is a compound comprising two or more residues of a molecule of the following formula (II)

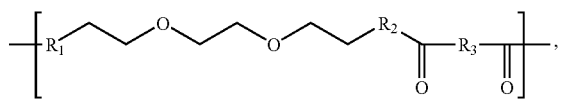

wherein $R_1$ and $R_2$ are selected from NH and O, and $R_3$ is selected from methyl, ethyl, propyl, $CH_2OCH_2$, and $(CH_2OCH_2)_2$, and wherein no more than three consecutively repeating ethyloxy groups.

Multiple labels attached to and separated by the above spacer may be may be conjugated with one Y-head or several Y-heads via a suitable linker, e.g. a water soluble polymers allowing multiple attachments, e.g. dextran. In some embodiments several Y-heads may be conjugated with several Z-tails via such polymer.

In one embodiment multiple detectable labels attached to one and the same conjugate molecule may be same detectable substances, in another embodiment the labels may be different detectable substances.

A Z-tail arrangement of labels has an advantage that (1) conjugates comprising multiple hydrophobic labels separated by a hydrophilic spacer molecule between the labels remain good solubility in water solutions, and (2) the labels are better accessible for binding agents, when binding agents are used to detect the conjugates.

A linker, L, is according to the invention a molecule that comprises a chain of at least 30 contiguous atoms, such as 30-150 atoms or more, e.g. 30, 45, 60, 90, 150, 300, 500 atoms or more. In one preferred embodiment preferably, L comprises 150 contiguous atoms. In some embodiments, a linker molecule comprises a linear chain of atoms wherein every two connected carbon atoms are followed by an atom of oxygen or nitrogen.

In one preferred embodiment L is a single linear polymer molecule; in one preferred embodiment L is conjugate molecule which comprises several different polymers conjugated together.

In one preferred embodiment the linear polymer comprises a chain of atoms wherein two consecutive carbon atoms are followed by a heteroatom selected from oxygen or nitrogen, e.g. such as a linker described below, or polyethylene glycol, etc.

There is a great variety of polymer molecules that may be used as linker L. Examples include polysaccharides such as dextrans, carboxy methyl dextran, dextran polyaldehyde, carboxymethyl dextran lactone, and cyclodextrins; pullulans, schizophyllan, scleroglucan, xanthan, gellan, O-ethyl-amino guaran, chitins and chitosans such as 6-O-carboxymethyl chitin and N-carboxymethyl chitosan; derivatized cellolosics such as carboxymethyl cellulose, carboxymethyl hydroxyethyl cellulose, hydroxyethyl cellulose, 6-amino-6-deoxy cellulose and O-ethylamine cellulose; hydroxylated starch, hydroxypropyl starch, hydroxyethyl starch, carrageenans, alginates, and agarose; synthetic polysaccharides such as ficoll and carboxymethylated ficoll; vinyl polymers including poly(acrylic acid), poly(acryl amides), poly (acrylic esters), poly(2-hydroxy ethyl methacrylate), poly (methyl methacrylate), poly(maleic acid), poly(maleic anhydride), poly(acrylamide), poly(ethyl-co-vinyl acetate), poly (methacrylic acid), poly(vinylalcohol), poly(vinyl alcohol-co-vinyl chloroacetate), aminated poly(vinyl alcohol), and co block polymers thereof; poly ethylene glycol (PEG) or polypropylene glycol or poly(ethylene oxide-co-propylene oxides) containing polymer backbones including linear, comb-shaped or hyperbranched polymers and dendrimers, including branched PAMAM-dendrimers; poly amino acids including polylysines, polyglutamic acid, polyurethanes, poly(ethylene imines), pluriol; proteins including albumins, immunoglobulins, and virus-like proteins (VLP), and polynucleotides, DNA, PNA, LNA, oligonucleotides and oligonucleotide dendrimer constructs; mixed polymers, i.e., polymers comprised of one or more of the preceding examples of polymers, co-block polymers and random co-polymers.

Properties of the chosen polymer can be modified to optimize performance, e.g. the length or branching can be optimized. Furthermore, the polymer may be chemically modified to carry various substituents. The substituents may be further chemically protected and/or activated, allowing the polymer to be derivatized further.

In one preferred embodiment the linker is a dextran or mixed polymer comprising dextran In another preferred embodiment the linker is a compound comprising two or more residues of a molecule of the following formula (II)

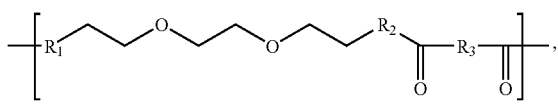

wherein $R_1$ and $R_2$ are selected from NH and O, and $R_3$ is selected from methyl, ethyl, propyl, $CH_2OCH_2$, and $(CH_2OCH_2)_2$, and wherein no more than three consecutively repeating ethyloxy groups.

Preferably, linker L comprises at least two residues of the above formula wherein both $R_1$ and $R_2$ are NH and $R_3$ is $CH_2OCH_2$. Preferably L comprises one or more units of the following formula (III)

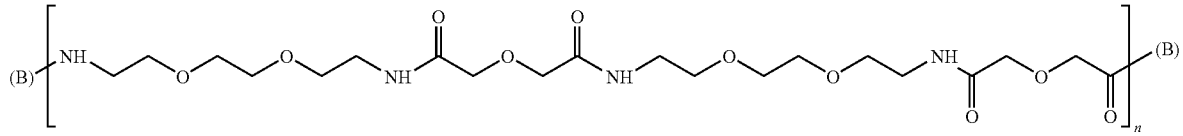

wherein n is an integer from 1 to 10, and (B) is a branching point. The L molecules of this formula and their synthesis are in detail described in WO2007/015168, which is incorporated herein by reference.

By the term "branching point" is meant a point in a polymer molecule wherein a branch, e.g. a side chain of the same polymer, or other molecules may be attached. In one embodiment the branching point (B) may be an atom, in another embodiment it may be a functional group or molecule through which molecules Y and Z may be directly or indirectly conjugated to L, e.g. via functional groups of Y or Z (i.e. directly), or via small bi-functional molecules (i.e. indirectly), e.g. amino acids, e.g cysteine, lysine etc.

Methods of conjugating polymers with different chemical substances, e.g. labels, are well known in the art and can be used to make conjugates of the invention. For example, the polymer may be activated with vinylsulfon and mixed with a detectable label and molecule of formula (II) to form the polymer conjugate. In other embodiments, aldehydes can used to activate a polymer, e.g. dextran, which is then mixed with a detectable label and molecule of formula (II). Yet another method of preparing polymeric conjugates is by using so called chemo selective coupling schemes for coupling the components together, e.g. molecules can be derivatized with thiol reactive maleimide groups before being covalent coupled to an thiol modified polymeric backbone. In some other embodiments, a molecule for formula (I) and detectable label can be attached to the polymer via a linker grouping. Examples of this method include the use of homobifunctional linker groupings such as glutaric dialdehyde, hexan di isocyanate, dimethylapimidate, 1,5-difluoro-2,4-dinitrobenzene, heterobifunctional cross binders like e.g. N-gamma-maleimidobytyroloxy succinimide ester, and zero length cross binders such as 1-ethyl-3-(3-dimethylaminopropyl)cabodiimide.

Methods of derivatization of molecules comprising one or more units of L30 are described in detail in WO2007/015168, which is incorporated herein by reference.

Exemplary conjugates comprising L30 repeats, such as L60 (2×L30 repeats), L90 (3×L30 repeats), L150 (5×L30 repeats), are described in EXAMPLES and shown in FIG. 1(3).

Use of Conjugate Molecules

The conjugate molecules of the invention may advantageously be used in detection of peroxidase activity in samples.

A peroxidase enzyme, such as horse radish peroxidase uses the conjugate molecules of the invention as a substrate, and in the presence of another substrate 3,3' diaminobenzidine and a peroxide compound, converts water soluble molecules of the conjugates to water insoluble. This may be observed as formation of precipitates (deposits) of the conjugates solid supports, or it may be detected as clouding of a clear solutions, wherein the precipitates is suspended in the solution. In case a peroxidase enzyme is immobilized on a solid support, formation of a deposit will be directed to a site of this support which comprises peroxidase activity. The deposit on a solid support or suspended precipitate in a solution may be detected directly, e.g. by eye observation, or by use of detection means, e.g. by detecting a detectable label of the precipitated conjugate molecule.

Peroxidase activity present in a sample may per se a target of detection by a method employing the described conjugate molecules. In some embodiments, the target of detection may be a molecule of an object that itself does not have peroxidase activity. In these embodiments, the target molecule or object should be first labeled with peoxidase activity to become detectable according to the invention.

Meaning of the term "target" in the context of the present invention is discussed in the below sections.

1. Method of Detection

In one aspect the invention relates to a method of detection of peroxidase activity in a sample, comprising I. incubating a sample supposedly peroxidase activity in a water solution comprising:
   d) a conjugate according to the invention,
   a) 3,3' diaminobenzidine, and
   b) a peroxide compound,
   thereby forming a precipitate of the compound;
II. detecting the precipitate of the compound in the sample, thereby detecting peroxidase activity in the sample.

In another aspect the invention relates to a method wherein a target in a sample, e.g. an object with peroxidase activity, biological marker, etc, wherein said target or sample immobilized onto a solid support, wherein said method comprises steps of a. incubating a sample supposedly comprising target with one or more binding agents comprising peroxidase activity, wherein said one or more binding agents is/are capable of direct or indirect binding to the target and form complex comprising the target and one or more binding agents, whereof at least one comprises peroxidase activity;
b. incubating the sample of (i) in a water solution comprising
   i. 3,3' diaminobenzidine,
   ii. a peroxide compound, and
   iii. a conjugate
c. detecting the deposited conjugate, and thereby detecting the target.

Embodiments of detection methods of the invention are discussed below.

Sample

The term "sample" means an amount of a material that shows what the rest of the material is or should be like, e.g. a sample of biological, chemical, environmental material, e.g. a sample of a body tissue, a sample of food, a soil sample. In one embodiment the sample is a biological sample.

A biological sample may be exemplified by:
1. a sample comprising suspended cells and/or cells debris, e.g. blood sample, suspension of cloned cells, body tissue homogenate, etc;
2. a sample comprising of intact or damaged cells of an animal body, a body tissue, smear or fluid or a sample of a tumor, e.g. a biopsy sample; It may be a fresh tissue sample or preserved tissue sample, e.g. a formalin fixed paraffin embedded tissue sample;
3. a sample comprising a living organism, e.g. a sample of a medium comprising an animal, plant, bacterium, fungi, etc;
4. a sample comprising viral particles, debris thereof, or viral products, e.g., a body smear comprising viral nucleic acids, proteins, peptides, etc;
5. a sample comprising a cell organelle(s);
6. a sample comprising natural or recombinant biological molecules, e.g. blood plasma sample, conditioned cell culture media, etc.

Examples of chemical samples include but not limited to samples of libraries of chemical compounds, e.g. peptide libraries. Examples of the environmental samples include, but not limited to soil, water or air samples and food samples.

The sample may in one embodiment be immobilized onto a solid support, e.g. a body tissue sample immobilized on a glass or plastic slide; a cell-free sample comprising biological molecules immobilized onto a nitrocellulose membrane, etc. The term "solid support" means a piece of any solid water insoluble material, e.g. a nitrocellulose membrane, glass slide etc. The support may in one embodiment be a one-molecular layer thick membrane or be a multi molecular layered piece of a material, e.g. plastic or glass. The target in this embodiment is immobilized on a surface of the support. In another embodiment the solid support may be a three-dimensional structure, e.g. a gel block or a mesh of fibers. In this embodiment the target is immobilized within the structure. In one embodiment, the solid support is a cellular membrane, e.g. the plasma membrane. The term "immobilized" means that a sample or target is not movable on or within the support or is movable to a very limited degree.

Examples of supports suitable for immobilizing the samples include but not limited to synthetic polymer supports, such as polystyrene, polypropylene, substituted polystyrene, e.g, aminated or carboxylated polystyrene; polyacrylamides; polyamides; polyvinylchloride; glass; agarose; nitrocellulose; nylon; polyvinylidenedifluoride; surface-modified nylon, etc. The invention relates to a solid support that is chemically inert under conditions described herein, i.e. the chosen support may not have any major influence on the results of detection by the method. Accordingly, any such inert support suitable for immobilizing a sample or target fitting the chosen assay format, e.g. for IHC, ELISA, blotting etc, may be selected.

In one embodiment, a sample may be itself solid, e.g. a sample of formalin fixed solid tissue (i.e. not a blood sample) and/or paraffin embedded tissue sample, e.g. a formalin fixed paraffin embedded sample of a solid tumor, a sample of a skin, lever, breast, lung, etc. In this embodiment, the sample itself may be accounted as solid support comprising an immobilized target.

Target

The term "target" means an object of interest (supposedly present in the sample) that can be characterized by particular physical and functional features. In the context of the invention, the term "target" relates to the whole pool of substantially similar entities of that object present in the sample, but not to every individual single unit of that object. The term "substantially similar" in the present context means that all entities of the pool possess the feature that makes them recognizable as the target. For example, in one embodiment the target may be a protein present in a sample including all molecules of that protein in the sample; in another embodiment the target may be a molecular complex or structure including the all molecular complexes or molecular structures of that kind in the sample; in another embodiment the target may be a viral particle or a bacterium including the total population of the viral particles or bacteria of the sample. Thus, the term target relates to a plurality of units of one particular kind in a sample. It is thus understood that the method described herein relates to visualizing a plurality of single units of a molecular target, i.e. the whole pool of target molecules in the sample, but not visualizing individual single units, e.g. single molecules, of this target.

In the field of medical diagnostic biological objects such as molecules, molecular complexes, structures, particles or organisms are often associated with characteristic features of a cell type, tissue, cellular structure, physiological condition, etc. and termed "biological marker" to designate a therapeutic target or characteristic molecular feature of a particular disease. In some embodiments of the invention, the term "target" is used interchangeable with the term "biological marker" and relates to a molecule, molecular complex, structure or particle that is characteristic for a particular cell type, tissue, physiologic condition, etc. Non-limited examples of such biological markers include but not-limited to particular nucleotide sequences, proteins or other biological molecules, e.g. carbohydrates or lipids, chromosomal or membrane structures, viruses, bacteria, microorganisms etc.

In one embodiment, the target is a polypeptide, nucleic acid, carbohydrate, lipid or a derivative thereof, molecular complex, particle, eukaryotic or prokaryotic cell or microorganism.

Among targets of chemical and environmental samples may be different pollutants, toxins, warfare substances, members of molecular libraries, industrial noxious waste, etc.

The target may be a part of a structure of a cell, e.g. a protein of the plasma membrane. In this embodiment, the cellular structure where the target is immobilized may be considered as a type of s solid support within context of the present invention.

In one preferred embodiment, the target is a biological marker related to cancer, e.g. a gene or a product thereof related cancer, e.g. nucleic acids and polypeptides of hormones and growth factors and their receptors, cell adhesion molecules signal transduction molecules, cell cycle regulation molecules, etc, e.g. genes and proteins of the group: PDGF, VEGF, TGF, HGF, FGF or EGF, their receptors and signal transduction molecules, genes and their products related to the JAK/STAT pathway or Akt1/PKB cell survival pathway, or 5-FU pathway, estrogen receptor ER and its gene (ERS1), etc.

In one embodiment, the target is a peroxidase enzyme present in a sample.

Target Site

The term "target site" in the context of the present invention means a site of a solid support or a site of solid sample, e.g. a solid tissue sample, comprising a target and peroxidase activity. In one embodiment the target site may a site of a sample or a site of a solid support which comprises a target, e.g. a molecule, virus, microorganism etc. labeled with peroxidase activity, i.e. the target does not itself has peroxidase activity, but said activity was directly or indirectly liked to the target. A peroxidase activity may be linked to the target via direct conjugation of a moiety of a peroxidase enzyme to said target ("moiety" in context of the invention means a functional portion of a molecule, e.g. a portion of a peroxidase enzyme that is capable of enzymatic activity of said peroxidase). Alternatively, a peroxidase activity may be linked to a target indirectly, e.g. via binding to the target of a peroxidase activity containing binding agent.

In one embodiment, a target may be a peroxidase enzyme itself, accordingly a site of a solid sample or a site of a solid support comprising this enzyme is a target site of the invention.

According to the invention, a conjugate molecule allows detecting a target in that the conjugate reports under conditions of the invention the presence of the target molecule in the environment by directly or indirectly giving off a signal associated with its label. Accordingly, the conjugate molecules of the invention in some embodiments are termed "conjugate molecules" or "conjugates".

Incubation

In some embodiments a sample, target, target site, a deposited conjugate may incubated in different media.

The term "incubating" means that a sample or target or a complex of a target with a binding agent, is maintained in a medium for a period of time, e.g. in a medium comprising a particular reagent that specifically interacts with a target, e.g. a binding agent that is capable of directly or indirectly binding to the target, etc. The period of time may vary from 10 seconds to 3 min or continues for a longer periods of time, for example 5-10 min, 10-20 min, 20-40 min, 40-60 min, 1-2 hours or longer, e.g. overnight. The incubating may be performed in different temperature conditions depending on different embodiments, e.g. the type of the target molecule to be detected or type of binding agent and/or conjugate used for the detection, etc. The term "incubating" in some embodiments may be interchangeably used with the term "washing", which usually used in conditions when a sample is incubated in a medium that lacks specific binding agent and serves to remove particular agents from the sample.

The invention in most embodiments relates to incubation times within a range of 10 seconds to 20 minutes.

Binding Agent

The term "binding agent" designates a molecule that is capable of direct or indirect binding to a target, wherein the term "directly" means that the binding agent has affinity to the target and is capable of specifically recognizing and interacting with the target and binding to it, wherein the term "indirectly" means that the binding agent does not have specific affinity to the target but has such affinity to a substance which is associated with the target and is capable of specifically binding to this substance. The binding agent which is capable of direct binding to a target is termed herein "first binding agent". The binding agent which is capable of indirect binding to a target is termed herein "second binding agent". The first binding agent is typically used to contact the sample. It may be comprised of any molecule which will specifically bind to the target supposedly present in the sample. The second binding agent may be e.g. any molecule that binds the first binding agent.

The detection system according to the invention may comprise other binding agents, e.g. a third, fourth, etc. binding agents. These binding agents may be used for recognition a label comprised by a deposited conjugate molecule. Use of such binding agents is particular advantageous when it is desirable to enhance a signal associated with the target, e.g. in case of a relatively low amount of the target in a sample.

The first, second and further binding agents according to the invention may be the members of a specific binding pair.

A number of different specific binding pairs are known in the art, these are the pairs of two different molecules which have mutual affinity for each other and are capable of specific binding to each other. Members of specific binding pairs suitable for use in practicing the invention may be of the immune or non-immune type.

Non-immune specific binding pairs include systems where the specifically binding to each other components share a mutual affinity for each other, but they are not antibodies. Exemplary non-immune binding pairs are biotin-avidin or biotin-streptavidin, folic acid-folate binding protein, complementary nucleic acids, receptor-ligand, etc. The invention also includes non-immune binding pairs which form a covalent bond with each other. Exemplary covalent binding pairs include sulfhydryl reactive groups such as maleimides and haloacetyl derivatives and amine reactive groups such as isothiocyanates, succinimidyl esters, sulfonyl halides, and coupler dyes such as 3-methyl-2-benzothiazolinone hydrazone (MBTH) and 3-(dimethyl-amino)benzoic acid (DMAB), etc.

Immune specific binding pairs may be exemplified by antibody/antibody systems or hapten/anti-hapten antibody or antigen/antibody systems. In one embodiment the immune specific binding pair may be an antibody/antibody binding pair comprising two or more antibody molecules having affinity to each other, for example a primary antibody and secondary antibody pair, wherein the primary antibody represents a first binding agent and the secondary antibody represents a second binding agent, or an antibody system comprising 3 or 4, or more antibody members. In other embodiments the immune specific binding pair may be represented hapten/anti-hapten system. For example, the first binding agent may be represented by a molecule comprising a hapten, e.g. a hapten labeled primary antibody, and the second binding agent may be represented by an anti-hapten antibody.

The term "hapten" designates a small molecule which can be considered as an isolated epitope to which an antibody can be made, although the hapten alone will not induce an immune response if injected into an animal, it must be conjugated to a carrier (usually a protein). As haptens are small molecules, multiple copies of a hapten may be attached to a large molecule, e.g. a polymer molecule, such as protein, nucleotide sequence, dextran, etc. Haptens may serve as convenient label molecules for assay formats where it is necessary or advantageous to amplify a signal. Thus, the bound multiple copies of a hapten provide for enhanced sensitivity, e.g. increased signal strength. Non-limited examples of suitable haptens include FITC, DNP, myc Digoxigenin, nitrotyrosine biotin, avidin, strepavidin and anti-dye antibodies to e.g. tetramethylrhodamine, Texas Red, dansyl, Alexa Fluor 488, BODIPY FL, lucifer yellow and Alexa Fluor 405/Cascade Blue fluorophores, or those described in US20080305497.

The term "antibody", as used herein, designates an immunoglobulin or a part thereof, and includes any polypeptide comprising an antigen-binding site regardless of the source, method of production, and other characteristics. The term includes for example, polyclonal, monoclonal, monospecific, polyspecific, humanized, single-chain, chimeric, synthetic, recombinant, hybrid, mutated, and CDR-grafted antibodies. A part of an antibody can include any fragment which can still bind antigen, for example, an Fab, F(ab)$_2$, Fv, scFv. The origin of the antibody is defined by the genomic sequence irrespective of the method of production.

Primary antibody, as used herein, refers to an antibody that specifically binds to a target molecule of a sample. In certain embodiments the primary antibody may be polymerized. Primary antibodies may be derived from any warm blooded species, e.g. mammals, birds.

Secondary antibody, as used herein, refers to an antibody that has an antigen binding domain that specifically binds to the primary antibody, or a hapten deposited in the target site, or hapten linked directly or indirectly to a primary antibody or another binding agent.

Tertiary antibody, as used herein, refers to an antibody that has an antigen binding domain that specifically binds to a secondary antibody or a hapten linked to a secondary antibody or a hapten linked to polymer conjugated to a secondary antibody, or hapten deposited in the target site.

Sometimes an antibody may function both as a secondary and a tertiary antibody.

Antibodies used in the invention, including primary antibodies, secondary antibodies and tertiary antibodies, may be derived from any mammal species, e.g., a rat, a mouse, a goat, a guinea pig, a donkey, a rabbit, horse, lama, camel, or any avian species e.g., chicken, duck.

Derived from any mammal or avian species, as used herein, means that at least a part of the nucleic acid sequence encoding a particular antibody originated from the genomic sequence of a specific mammal, e.g., a rat, a mouse, a goat, or a rabbit or a specific bird e.g., chicken, duck. The antibody may be of any isotype, e.g., IgG, IgM, IgA, IgD, IgE or any subclass, e.g., IgG1, IgG2, IgG3, IgG4.

In certain embodiments the primary antibody contains an antigen binding region which can specifically bind to a biological marker expressed by cells comprising a biological sample. The marker may be expressed on the cell surface or within the cell membrane, i.e., on the interior of the cell, e.g., within the cytoplasm, within the nucleus, within the endoplasmic reticulum. In some embodiments the biological marker is secreted from the cell and thus is present in solution, e.g., in cell culture media, in blood or plasma.

In certain embodiments, the secondary antibody contains an antigen binding region which specifically binds to the primary antibody, e.g., the constant region of the primary antibody. In certain embodiments, the secondary antibody is conjugated to a polymer. In some embodiments, the polymer is conjugated with 2-20 secondary antibodies, such as 5-15 secondary antibodies. In other embodiments, the polymer is conjugated with 1-10 secondary antibodies, such as 2, 3, 4, 5, 6, 7, 8, or 9 secondary antibodies.

In certain embodiments, the tertiary antibody contains an antigen binding region which specifically binds to the secondary antibody, e.g., a constant region of the secondary antibody, or a hapten linked to the secondary antibody or a polymer conjugated to the secondary antibody. In certain embodiments, the tertiary antibody is conjugated to a polymer. In some embodiments, the polymer is conjugated with 1-20 tertiary antibodies. In other embodiments, the polymer is conjugated with 1-5 tertiary antibodies, such as 2, 3, or 4 tertiary antibodies.

The antibodies that may be used in the methods and compositions of the invention include monoclonal and polyclonal antibodies, engineered antibodies including chimeric, CDR-grafted and artificially selected antibodies produced using phage display or alternative techniques.

Various techniques for producing antibodies have been described, see, e.g., Kohler and Milstein, (1975) *Nature* 256:495; Harlow and Lane, *Antibodies: a Laboratory Manual*, (1988) (Cold Spring Harbor Press, Cold Spring Harbor, N.Y.) incorporated herein by reference. Techniques for the preparation of recombinant antibody molecules is described in the above references and also in, for example, EP 0623679; EP 0368684; and EP 0436597. Antibodies may be produced recombinantly or synthetically. Nucleic acids encoding antibodies may be isolated from a cDNA library. Nucleic acids encoding antibodies may be isolated from a phage library (see e.g. McCafferty et al. 1990, Nature 348:552, Kang et al. 1991, *Proc. Natl. Acad. Sci. USA* 88:4363; EP 0 589 877 B1). Nucleic acids encoding antibodies can be obtained by gene shuffling of known sequences (Mark et al. 1992, *Bio/Technol.* 10:779). Nucleic acids encoding antibodies can be isolated by in vivo recombination (Waterhouse et al. 1993, *Nucl. Acid Res.* 21:2265). The antibodies used in the methods and compositions of the invention include humanized immunoglobulins (U.S. Pat. No. 5,585,089, Jones et al. 1986, *Nature* 332:323).

The antibodies may be altered antibodies, e.g an antibody comprising an effector protein such as a toxin or a label, e.g., a detectable substance.

In one embodiment of the invention, the antibody is represented by the Fab region of an antibody.

In another embodiment, the binding agents may be members of a non-immune specific binding pair, such as a complementary nucleotide sequence pair, or a pair of two nucleic acid analog molecules having mutual affinity.

A binding agent comprising a nucleic acid or nucleic acid analog molecule, e.g., a DNA molecule, an RNA molecule, a PNA molecule, may be useful for example for detection of nucleic acid targets.

Nucleic acid sequences may be synthesized chemically or produced recombinantly in cells (see e.g. Sambrook et al. (1989) *Molecular Cloning: A Laboratory Manual*, 2nd ed. Cold Spring Harbor Press). In some embodiments, the binding agent is comprised of a peptide nucleic acid (PNA). A peptide nucleic acid is a nucleic acid molecule in which the deoxyribose or ribose sugar backbone, usually present in DNA and RNA is replaced with a peptide backbone. Methods of making PNAs are known in the art (see e.g. Nielson, 2001, *Current Opinion in Biotechnology* 12:16) (hereby incorporated by reference). In other embodiments, the binding agent is comprised of locked nucleic acids (LNA) (Sorenson et al. 2003, *Chem. Commun.* 7(17):2130).

The binding agent, in some embodiments, may comprise at least one sequence that specifically hybridizes to a target sequence in a biological sample, e.g. a nucleic acid sequence such as a genomic DNA sequence or an mRNA sequence, under specific conditions of stringency. As used herein, the term "hybridization under stringent conditions," is intended to describe conditions for hybridization and washes under which nucleotide sequences that are significantly complementary to each other remain bound to each other. The conditions are such that sequences at least 70%, at least 80%, at least 85-90% complementary remain bound to each other. The percent complementary is determined as described in Altschul et al. (1997) *Nucleic Acids Res.* 25:3389-3402 (hereby incorporated by reference).

Specified conditions of stringency are known in the art and can be found in *Current Protocols in Molecular Biology*, John Wiley & Sons, Inc. (Ausubel et al. 1995 eds.), sections 2, 4, and 6 (hereby incorporated by reference). Additionally, specified stringent conditions are described in Sambrook et al. (1989) *Molecular Cloning: A Laboratory Manual*, 2nd ed. Cold Spring Harbor Press, chapters 7, 9, and 11 (hereby incorporated by reference). In some embodiments, the hybridization conditions are high stringency conditions. An example of high stringency hybridization conditions is hybridization in 4× sodium chloride/sodium citrate (SSC) at 65-70° C. or hybridization in 4×SSC plus 50% formamide at 42-50° C., followed by one or more washes in 1×SSC, at 65-70° C. It will be understood that additional reagents may be added to hybridization and/or wash buffers, e.g., blocking agents (BSA or salmon sperm DNA), detergents (SDS), chelating agents (EDTA), Ficoll, PVP, etc.

In some embodiments, the binding agents may hybridize to a target sequence in a sample under moderately stringent conditions. Moderate stringency, as used herein, include conditions that can be readily determined by those having ordinary skill in the art based on, for example, the length of the DNA. Exemplified conditions are set forth by Sambrook et al. *Molecular Cloning: A Laboratory Manual*, 2d ed. Vol. 1, pp. 1.101-104, Cold Spring Harbor Laboratory Press (1989) (hereby incorporated by reference), and include use of a prewashing solution of 5×SSC, 0.5% SDS, 1.0 mM EDTA (pH 8.0), hybridization conditions of 50% formamide, 6×SSC at 42° C. (or other similar hybridization solution, such as Stark's solution, in 50% formamide at 42° C.), and washing conditions of 60° C., 0.5×SSC, 0.1% SDS.

In some embodiments, the binding agents hybridize to a target sequence in a sample under low stringent conditions. Low stringency conditions may include, as used herein, conditions that can be readily determined by those having ordinary skill in the art based on, for example, the length of the DNA. Low stringency may include, for example, pretreating the DNA for 6 hours at 40° C. in a solution containing 35% formamide, 5×SSC, 50 mM Tris-HCl (pH 7.5), 5 mM EDTA, 0.1% PVP, 0.1% Ficoll, 1% BSA, and 500 μg/ml denatured salmon sperm DNA. Hybridizations are carried out in the same solution with the following modifications: 0.02% PVP, 0.02% Ficoll, 0.2% BSA, 100 μg/ml salmon sperm DNA, 10% (wt/vol) dextran sulfate, and 5-20×10$^6$ CPM binding agent is used. Samples are incubated in hybridization mixture for 18-20 hours at 40° C., and then washed for 1.5 h at 55° C. in a solution containing 2×SSC, 25 mM Tris-HCl (pH 7.4), 5 mM EDTA, and 0.1% SDS. The wash solution is replaced with fresh solution and incubated an additional 1.5 h at 60° C.

Other embodiments of the invention may relate to binding agents which are or which may include peptide sequences, e.g. peptide sequences derived from different proteins, e.g., nucleic acid binding domains of different proteins, fragments of ligands of different cellular and nuclear receptors and their derivatives. Some examples of such binding agents may be c1q protein of the classical pathway of the complement cascade which can bind to an antibody constant region, a MHC molecule, e.g., MHC class I and MHC class II and non conventional MHC, a molecule having a specific binding partner, such as molecules involved in cellular signaling pathways such as molecules having leucine zipper domains, e.g., fos/jun, myc, GCN4, molecules having SH1 or SH2 domains, such as Src or Grb-2; an immunoglobulin receptor, e.g., an Fc receptor; a chimeric protein, i.e., a protein engineered to combine the features of two or more specific binding partners, e.g., a leucine zipper could be engineered into a Fc region of an antibody, an SH2 domain could be engineered to be expressed in a Fc region of an antibody. In other embodiments, fusion proteins can be engineered comprising an Fc portion of an antibody with a substituted variable domain. However, this is just a list of non-limiting examples of substances that can be used as binding agents for the purposes of the present invention. The binding agent may also be small molecules which can bind specifically to certain structural units of large biological molecules.

In one embodiment the binding agent is represented by an antibody derivative, preferably the antigen binding domain Fab. The binding agents that are represented by the Fab regions of primary and/or secondary antibodies that are conjugated with at least one moiety of HRP in some embodiments may be preferred before the corresponding whole antibody binding agents. Such binding agents are more compact molecules than the whole antibody binding agents, and this is advantageous for obtaining a more condensed deposition of a conjugate in the proximity to the target site. This may be beneficial for precision of detection of the target. This may be of particular advantage when the method of the invention is used for immunohistochemical detection of target molecules, structures or particles in biological samples comprising cells. Immunostaining of target molecules in such samples is especially crisp when binding agents used are Fab molecules conjugated with a moiety of HRP or they comprise a Fab region and HRP. Another advantage of using HRP conjugated Fab binding agents is that these binding agents are relatively small in size and therefore have better assess to hidden or masked targets in biological samples that are typically difficult to access when larger antibody-based binding agents are used.

The amount of binding agent used for the detection of a target in an assay using the method of the invention may be significantly reduced compared to the amounts routinely used in the methods of prior art, such as e.g. 100-1000 times reduced, as the invention provides for a strong amplification of a detectable signal associated with the target.

The amount of an antibody used for detection of a target in a sample is very much dependent on the antibody, target, or sample. Therefore, this amount should be individually defined in every particular case, which is a routine procedure known to a skilled in the art. When defined, however, the amount of the antibody used for detection of a target by the present method may be up to 1000 times compared to the amount which would be required by most current immuno-detection procedures. Possibility of multiple amplification of a signal associated with the target, i.e. first in step of deposition of a conjugate of the invention, and then in step of labeling the deposited conjugate, makes the detection by the present method also less dependent on the affinity of a primary binding agent, i.e. affinity to the target, because even a weak binding of the binding agent to a target may be detected.

Amplification of a specific signal, i.e. target associated, may be may be further increased by repeating deposition step and increasing the amount of deposited conjugate in target sites. For example, a conjugate deposited in step (ii) of method of the invention may comprises a detectable label that can be specifically recognized by a binding agent comprises peroxidase activity; this sample may be incubated again in a deposition media comprising the same or another conjugate molecule, increasing thus the site associated deposit. Notably, in this way, there may be performed up to 50 rounds of the same target sites directed conjugate deposition without any noticeable non-specific deposition, e.g. in the areas of the sample or solid support with no non-target sites. As mentioned, the conjugate molecule to be deposited on the second and further rounds of deposition may be the same conjugate, i.e. as used on the first round, or it may be a different conjugate molecule. This second or further conjugate molecules may be molecules that may produce more robust signal or comprise an increased amount of detectable labels; in this way the target site associated signal may be alternatively or/and further enhanced.

Accordingly, the method also provides for flexibility of the detection procedure, and for reproducible detection of targets in a huge variety of samples immobilized onto a solid support. The method is very advantageous for immunochemical detection of targets in challenging samples such as histological samples, as it provides for a very crisp and specific immunochemical labeling of molecular targets and thus facilitates interpretation and quantification of the sample content.

Peroxidase Activity

The term "peroxidase activity" relates to an enzymatic activity catalyzing a reaction of the form:

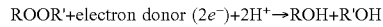

ROOR'+electron donor $(2e^-)+2H^+ \rightarrow ROH+R'OH$

An enzyme having the peroxidase activity is termed herein "peroxidase" or "enzyme with peroxidase activity". For many peroxidases the optimal substrate is hydrogen peroxide, but others are more active with organic hydroperoxides such as organic peroxides. The nature of the electron donor is very dependent on the structure of the enzyme, e.g. Horseradish peroxidase (HRP)/EC 1.11.1.7) can use a variety of organic compounds both as electron donors and acceptors. HRP has an accessible active site, and many compounds can reach the site of the reaction.

The peroxidase activity may be represented by a molecule of a peroxidase enzyme which is directly or indirectly linked to the molecule of a binding agent, or a fragment of the enzyme conflated with the enzymatic activity, e.g. 51% to 99.9% of the full size of the peroxidase molecule, or less than 51%.

A binding agent of the invention may be directly or indirectly conjugated with one or more peroxidase moieties, (the term "moiety" in the present content means a whole molecule of a peroxidase, or a portion of said molecule capable of peroxidase enzymatic activity). Molecules of both or either first and/or second binging agents may be conjugated with one or several functionally active moieties of a peroxidase. In one embodiment at least one molecule of a first binding agent may be conjugated with one or more peroxidase moieties; in another embodiment at least one molecule of a second binding agent may be conjugated with one or more peroxidase moieties. Molecules of third and further binding agents may also be conjugated with a peroxidase. The term "directly conjugated" means that the enzyme moiety is linked to the molecule of a binding agent via a chemical bond. The term "indirectly conjugated" means that the peroxidase is linked to the molecule of a binding agent via a linking molecule, which has one chemical bond with binding agent and another chemical bond with peroxidase. Embodiments of linking molecules are discussed below. Methods of conjugating enzyme moieties are well known in the art.

In one embodiment the moiety of proxidase is a moiety of HRP, e.g. the whole HRP molecule a fragment thereof that is capable of the HRP enzymatic activity, it may also be a recombinant protein comprising the part of HRP that possesses the enzymatic activity, etc. In another embodiment the peroxidase may be soybean peroxidase (SP).

Non-limiting examples of binding agents which comprise an enzyme with peroxidase activity may be a primary or secondary antibody molecule or a derivative thereof, e.g. a Fab, conjugated with one or more moieties of the full-length HRP, and nucleic acid binding agents conjugated with HRP. Such binding agents may bind directly or indirectly to targets and form thereby complexes each comprising a target and one or more molecules of binding agents that comprise an enzyme with peroxidase activity.

In one embodiment the binding agent is a conjugate comprising one, or two or more peroxidase moieties that are directly linked to the binding agent, e.g. an antibody molecule linked to one or more HRP moieties. In another embodiment the binding agent is a conjugate that comprises two or more peroxidase moieties that are linked to the binding agent indirectly, e.g. a conjugate wherein one or more molecules of an antibody and one or more HRP moieties independently linked to a backbone polymer, i.e. a binding agent wherein the enzyme with peroxidase activity is indirectly linked to the binding agent, i.e. the antibody. The number of HRP per molecule of binding agent may vary from 1 to 10 or be even higher, e.g. 20-50 or be even higher.

In some embodiments, small conjugate molecules of binding agents, e.g. single antibody molecules or their Fab regions that are conjugated with one, or two to ten moieties of a peroxidase, e.g. HRP, may be preferred. Such binding agents are relatively compact molecules, and this feature may be advantageous for detecting hidden targets, e.g.

individual single target molecules, structures or particles in complicated biological samples comprising cells. In other embodiments, large conjugates comprising a binding agent and tens to hundreds enzyme moieties may be preferred. Such binding agents may be advantageous e.g. in cases where very fast target detection is concerned or obtaining large deposits per individual target site are desirable.

A site of a solid support comprising peroxidase activity is termed herein "target site". In one embodiment the target site comprises peroxidase activity, such as a moiety of a peroxidase enzyme, which is directly immobilized onto or within a solid support. In another embodiment the target site comprises peroxidase activity which is immobilized onto or within a solid support indirectly, i.e. a moiety of a peroxidase enzyme is linked to a binding agent capable of directly or indirectly binding to a target that is immobilized onto or within a solid support. The latter are non-limited examples of the target site of the invention.

Incubation Media

A sample comprising a target may be incubated in different incubation media. The term "incubation medium" means in the present context a solution comprising particular compounds where a sample is maintained during a certain period of time (termed herein "incubation time") in order to allow a desirable reaction between the particular compounds of the solution and the sample taking place.

Time for maintaining/incubating the sample in an incubation medium, i.e. incubating time, may vary depending on the embodiment from approximately 3 seconds to approximately 3 min, e.g. around 10 seconds, 20 seconds, 30 seconds, 1 minute, 2 minutes, etc., for example 3-10 minutes, 10-20 minutes, 20-40 minutes, 40-60 minutes, 1-2 hours or longer, e.g. overnight. In one embodiment, the incubating time at all steps of the detection procedure may have the same duration, i.e. every incubating may lasts 1 min, 2 min, 3 minutes, 5 minutes, 10 minutes, etc. In another embodiment, the incubating time may vary from one step to another, e.g. incubating the sample in a media comprising a binding agent may last 1 minutes, incubating the sample in a media comprising 3',3-diaminobenzidine (DAB), a conjugate, and a peroxide compound may lasts 2 min minutes, incubating the sample in a media for the detection of the conjugate deposits may lasts 5 minutes, etc.

Incubating may be performed in various temperature conditions, depending on the type of target, binding agent, conjugate, etc. The detection procedures are mainly temperature independent, however, if desired, the temperature may be used for regulating of duration of the incubating time, e.g. lower temperatures may used to prolong the incubating time, and, vice versa, higher temperatures may be used to shorten the time for incubating.

According to the method, a sample comprising a target is sequentially incubated with different agents wherein the agents are dissolved in aqueous media. Compositions of incubation media are adjusted according to the purpose of each incubation.

On step (i) of the method of the invention the sample is incubated with one or more binding agents. Accordingly, in one aspect, the invention relates to a medium comprising a binding agent comprising an enzyme with peroxidase activity capable of directly or indirectly binding to a single unit of a target and thereby forms a target site. This medium is termed herein "first incubation medium" or "target incubation medium".

First incubation medium may be any liquid media, preferably aqueous media, where the chosen binding agent is soluble and is capable of binding to the target unit. Basically, the first incubation media is a buffered aqueous solution of one or more binding agents that has pH in the range from 4 to 9. In some embodiments the first incubation media may comprise an organic or inorganic salt. The inorganic salt may be selected form e.g. sodium chloride, magnesium chloride, potassium chloride, calcium chloride, sodium phosphate, or ammonium sulfate. The organic salt may be selected from e.g. sodium acetate, ammonium acetate or imidazole salts, e.g. imidazole hydrochloride, etc.

The amount of salt in a first incubation medium may range from approximately $10^{-3}$ M to saturation, e.g. from approximately 20 mM to approximately 200 mM, or from approximately 50 mM to approximately 500 mM. In one preferred embodiment, the media may comprise salt in the amount from approximately 10 mM to 500 mM. In another preferred embodiment the medium may be free of salt.

As mentioned, typically, the pH value of first incubation media may vary from about 4 to about 9, such as between pH 3.5 and pH 9.5, e.g. between pH 5 and pH 7, between pH 5.5 and pH 6.5 or between pH 6.5 and 7.5, or between pH 7 and pH 8, or between pH 7.5 and pH 8.5, or pH 8 and pH 9. Any buffer with a suitable buffer capacity may be used, e.g. phosphate buffered saline (PBS) and imidazole buffer. Other suitable buffers may be found in Good, Nebr., et al (1966) Hydrogen ion buffers for biological research. Biochem. 5(2), 467-477. The pH value of the media may be essential for binding of binding agent to the target; it may be optimized depending on the nature of the binding agent and the target.

In some embodiments the first incubation media may comprise an organic modifier (by the term "organic modifier" is meant any non water solvent), e.g. N-Methyl pyrolidone (NMP), dimethylsulphoxide (DMSO), mono- and diethylene glycol, sulpholane, N,N-dimethylformamide (DMF), polyethylene glycol (PEG), propylene glycol, etc. The amount of the organic modifier may vary from around 1% to around 20% (v/v or w/v), or, in some embodiments, be higher than 20%.

In some embodiments the first incubation media may comprise a detergent, e.g. polyethylenglycol-p-isooctyphenyl ether (NP-40)) or a surfactant (e.g. selected from the surfactants based on polyoxyethylene sorbitanmonolaurate (Tween), or a surfactant based on block copolymers (pluronic etc.), etc. The amount of the detergent may vary from about 0.001% to about 5%/v/v or w/v).

In some embodiments the first incubation media may comprise the binding agent stabilizing agent, e.g. bovine serum albumin or dextran. The amount of the stabilizing agent may vary from 0.01% to 20% (w/v).

In some embodiments the first incubation media may comprise an ion chelator (e.g. ethylene diamine tetra acetic acid (EDTA) or ethylene diamine hydroxyl phenylacetic acid type chelator (EDHPA), etc.). The amount of the chelator may vary from about $10^{-9}$ M to about $10^{-6}$ M.

In some embodiments, the first incubation media may comprise one or more blocking agents for saturating non-specific binding sites, i.e. sites of the solid support that do not comprise the target. Some non-limiting examples of blocking agents suitable for different embodiments, may be the Denhard's solution, bovine serum albumin, skimmed milk, etc.

Because of the invention contemplates a great variety of species of targets, binding agents and assay formats, composition of the first incubation media may vary and should be adjusted for every particular embodiment using the knowledge of the art. Some non-limited examples of the first incubation media are described in Examples.

In some embodiments, the invention relates to media for depositing conjugate molecules at target site where the deposited conjugates serve as conjugates informing about the presence of a target in these sites. This media is interchangeably termed herein "deposition media" or "second incubation media".

Deposition media of the invention is liquid media, preferably aqueous media.

In one embodiment the deposition media is a buffered aqueous medium having pH ranging from about 4 to about 9, comprising
(i) a conjugate;
(ii) a peroxide compound, and
(iii) 3,3"-diaminobenzidine (DAB)

In another embodiment, the deposition media is a buffered aqueous medium having pH ranging from about 4 to about 9, comprising
(i) a conjugate and
(ii) a peroxide compound.

Any buffer with a suitable buffer capacity may be used, e.g. phosphate buffered saline (PBS) and imidazole buffer. Other suitable buffers may be found in Good, Nebr., et al (1966) Hydrogen ion buffers for biological research. Biochem. 5(2), 467-477. The pH value of the media may be essential for depositing the conjugate; it may be optimized depending on the nature of the conjugate.

The deposition media may further comprise an organic or inorganic salt.

The inorganic salt may be selected form e.g. sodium chloride, magnesium chloride, potassium chloride, calcium chloride, sodium phosphate, or ammonium sulfate, etc.

The organic salt may be selected form e.g. sodium acetate, ammonium acetate or imidazole salts, e.g. imidazole hydrochloride, etc.

The amount of salt in the deposition media may range from approximately $10^{-3}$ M to saturation, e.g. from approximately 20 mM to approximately 200 mM, or from approximately 50 mM to approximately 500 mM. In one preferred embodiment, the media may comprise salt in the amount from approximately 10 mM to 500 mM. In another preferred embodiment the medium may be free of salt.

The deposition media may in different embodiments further comprise:
(i) an organic modifier and/or
(ii) an enzyme enhancer, and/or
(iii) an iron chelator, and/or
(iv) a detergent, and/or
(v) an anti-microbial agent The organic modifier may be present in the media in the amount from around 1% to around 20% (v/v or w/v), however, in some embodiments higher concentrations of the organic modifier may be required. The organic modifier may for example be polyethylene glycol (PEG). Other examples include but not limited to organic modifiers selected from the group essentially consisting of C1-C4, i.e. lower, alcohols, N-Methyl pyrolidone (NMP), dimethylsulphoxide (DMSO), mono- and diethylene glycol, sulpholane, N,N-dimethylformamide (DMF). In some embodiments it may be advantageous to use polyethylene glycol (PEG), e.g. PEG2000, or propylene glycol. The amount of polyethylene glycol in the media in these cases may vary from about 0.1% (v/v) to about 20% (v/v), for example from about 1% (v/v) to about 15%, such as 5-10% (v/v).

By the term "enzyme enhancer" is meant any compound which enhances the catalytic activity of peroxidase. Such enzyme enhancer may be selected from the group essentially consisting of phenylboronic acid derivatives and divalent metal ions such as nickel or calcium. The amount of the enzyme enhancer may vary from about $10^{-17}$ to about $10^{-3}$ M.

The iron chelator may be ethylene diamine tetra acetic acid (EDTA) or ethylene diamine hydroxyl phenylacetic acid type chelator (EDHPA). Concentration of the iron chelator may vary from about $10^{-9}$ to about $10^{-6}$ M.

The detergent may be selected from polyethylenglycol-p-isooctyphenyl ether (NP-40), a surfactant selected from the surfactants based on polyoxyethylene sorbitanmonolaurate (Tween), or a surfactant based on block copolymers (pluronic etc.). Concentration of the detergent may vary from about 0.001% to about 5%.

According to the invention the deposition media is a stable solution. The term "stable" in the present context means that the capability of the media to serve as reaction media for the peroxidase-mediated conjugate deposition remains to be essentially unchanged during substantial periods of time; such as the media may be prepared and kept for at least 4 hours at room temperature before the use. The deposition media may also be prepared and preserved for longer periods of time. To prolong the shelf-life of the media it may be useful to store the media at temperatures below 20° C., e.g. at 4-10° C., and/or to add to the media an anti-microbial compound. The anti-microbial compound may be any anti-microbial compound commonly used for such purpose, e.g. sodium azid, Proclin™ or Bronidox®.

Concentration of the conjugate in the media may vary from about $10^{-10}$ M to about $10^{-2}$ M, depending on the nature of the conjugate. For example from about $10^{-10}$ M to about $10^{-6}$ M when the conjugate is radioactive, an enzyme or member of a specific binding pair; for example from about $10^{-9}$ M to about $10^{-5}$ M when the conjugate is fluorescent or member of a specific binding pair; for example from about $10^{-5}$ M to about $10^{-2}$ M when the conjugate is a chromogen.

The media according to the invention comprises a peroxide compound. The peroxide compound may be selected from organic peroxides such as tert-butyl peroxide, ditert-butyl peroxide, peracetic acid, or it may be an adduct of hydrogen peroxide, such as hydrogen peroxide urea adduct. In some embodiments hydrogen peroxide ($H_2O_2$) is a preferred peroxide compound. The amount of $H_2O_2$ in the media may vary from 1.5 mM to 150 mM in different embodiments, e.g. from about 6 mM to about 100 mM, from about 5 mM to about 50 mM, from about 10 mM to about 15 mM, etc.

In one preferred embodiment the amount of $H_2O_2$ in the deposition media is more than 5 mM, e.g. from 5.1 mM to 65 mM, such as between 5.2 mM and 55 mM, such as from 5.3 mM to 45 mM, such as between 5.4 mM and 35 mM, such as from 5.5 mM to 25 mM, such as from 5.6 mM to 15 mM.

The amounts of DAB in the deposition media may vary depending on amount of $H_2O_2$ in the deposition media. In some embodiments DAB may present in the deposition media an amount that is less than 1 mM, e.g. between 0.25 mM and 0.85 mM, with the proviso that the amounts of $H_2O_2$ in this deposition media is higher than 5.5 mM e.g. from 5.6 mM to 56 mM.

Preferably, the amount of DAB in the deposition media is more than 1.4 mM, e.g. between 1.5 mM and 6 mM. This amount of DAB provides for a specific and abundant deposition of conjugate molecules from the deposition media comprising $H_2O_2$ in its widest concentration range, i.e. from 1.5 mM to 159 mM. The amounts of DAB from 3 mM to 6 mM provide for most specific and abundant deposition of conjugate molecules, which ensures both crispness and intensity of the final staining of the conjugate deposits, e.g. in immunohistochemical detection. However, the amounts of DAB ranging from 1.5 mM to 3 mM may also be used, despite of this amounts provide for a more blurry but still strong signal than the amounts within the range from 3 mM to 6 mM, which may be advantageously used in detection of low abundance targets in some embodiments. In such embodiments to enhance saturation of target sites with deposited conjugate, the duration of incubation of sample in the deposition media may be prolonged, e.g. to 3-5 min compared to 1 min incubation at higher amounts of DAB. However, as mentioned, the crispness of the final staining of the target will be significantly reduced.

The deposited conjugates may be detected directly, e.g. by observing color or fluorescent light emanating from target sites, or the deposits may be detected indirectly by using a detection media. Accordingly, in one aspect, the invention relates to a detection media which is a medium where a sample comprising the deposited conjugate is incubated in order to detect a detectable label of the deposited conjugate.

The detection media may any media allowing detecting and/or visualizing labels of the deposits of conjugate in a sample, in particular labels that cannot be visualized directly, e.g. via microscopic observation, e.g. a label being a member of a specific binding pair. Visualization of such conjugate deposits may be done using one or more steps following the deposition, wherein the first step may comprise incubation of the sample (comprising deposited conjugate) with an agent capable of specifically binding to the detectable label of the deposits e.g. with a third or further binding agents (described above).

Requirements to the composition of the conjugate detection media are the same as for target detection media: the chosen binding agent should be soluble in the media and capable of binding to the deposited conjugate/target. Accordingly, an incubation medium for detection of the conjugate may have the same or a similar composition as a target incubation medium, which embodiments are described above. Typically, it is a buffered aqueous solution comprising a binding agent capable of binding a detectable label of the deposited conjugate and one or more ingredients discussed above.

In one embodiment, the detection medium is medium for visualization of the conjugate deposits, e.g. an enzyme substrate solution or a color developing solution. This kind of detection media may be any suitable medium known in the art which is selected for every particular embodiment (i.e. the nature of detectable label associated with the deposits) following the instructions of the art.

The invention also relates to washing media, e.g. washing media between step (i) and (ii), between step (ii) and step (iii) of the method. Typically, a washing medium will be a medium of the same or similar composition as one that has been used for incubating of the sample in the step preceding the washing step, wherein the washing media lacks the active ingredient, i.e. a particular agent of the incubation step, e.g. a binding agent, a conjugate molecule, etc.

In one embodiment, the invention relates to a media for quenching the endogenous peroxidase activity. This type of media may be any media suitable for this purpose that is routinely used in the art.

Composition

In one embodiment the invention relates to a composition comprising a conjugate molecule of the invention. It is understood that the term "composition comprising a conjugate molecule of the invention" also includes compositions comprising an intermediate of the synthesis of conjugate molecules of the invention, e.g. such as mentioned in Table 1 of the EXAMPLES.

In one embodiment the composition is a water solution comprising a conjugate molecule of the invention. Non-limited examples of a water solution comprising a conjugate molecule of the invention may be media described above in the EXAMPLES.

In one embodiment a composition comprising a conjugate of the invention is a part of a kit-of-parts of the invention.

Kit-of-Part

The kit-of-part of the invention is a kit-of-parts for detecting of a target in a sample.

Because of method of the invention is suitable for detection of a huge variety of targets in a variety samples in a variety assay formats, kits-of-parts of the invention may comprise many different items, however all kits-of-parts of the invention comprises a composition comprising a conjugate molecule of the invention. The following are some non-limited exemplary embodiments of a kit-of-parts of the invention.

In one embodiment, the kit-of-parts may comprise:
(i) a composition comprising a conjugate as any of the defined above; and
(ii) one or more binding agents capable of direct or indirect binding to a target, wherein binding agents may be any binding agents described herein.

In another embodiment the kit-of parts may comprise:
(i) a conjugate as any of the defined above; and
(ii) a water composition comprising DAB.

In another embodiment the kit-of parts may comprise
(i) a conjugate, or a composition comprising a conjugate; optionally
(ii) a water composition comprising DAB;
(iii) a binding agent capable of specifically binding to the detectable label of the conjugate.

In another embodiment, the kit-of-parts may comprise
(i) any of the items or all items of the above embodiments;
(ii) means for visualization the conjugate deposits.

Suitable binding agents are in detail described above. In particular, in one embodiment the binding agent is or comprises an amino acid sequence, a nucleic acid sequence or nucleic acid analog sequence.

In particular in one embodiment, a binding agent of a kit-of-parts of the invention may be or may comprise an antibody or a derivative thereof. In one embodiment, the antibody binding agent may be or may comprise a F(ab)'1 fragment of an antibody. The F(ab)'1 may be in one embodiment be of a mouse antibody, in another embodiment it may be of a rabbit antibody, in another embodiment it may be of a swine antibody or of a goat antibody. The antibody species mentioned are just non-limited examples of suitable antibodies for use as binding agent of the invention. In one embodiment the antibody is labeled with a moiety of an enzyme, or any of the detectable labels described above, e.g. hapten. The binding agent may comprise at least one moiety of horseradish peroxidase HRP or Soybean peroxidase (SP). In one embodiment the binding agent comprises two moieties of HRP or SP:

In another embodiment the binding agent may be or may comprise a labeled or unlabeled nucleic acid sequence or nucleic acid analog sequence.

Means for visualization of conjugate deposits are any means that are suitable for visualization a particular detectable label associated with the deposited conjugate. Embodiments of the means for visualization the conjugate deposits include reagents for enzymatic labeling of targets, e.g.

enzymes such as HRP or alkaline phosphatase, their substrates and substrate solutions, means for enhancement of a signal associated with label of the conjugate, e.g. amplification solutions other than described herein.

Assay Formats

The method of the invention may be performed in a great variety of assay formats. Some non-limited embodiments of such assay formats are described below.

Target molecules comprised by cells of a cell suspension may be detected employing the method described above in any suitable assay format, for example in flow cytometry (FC), or ELISA, or immunohytochemistry (IHC), or in situ hybridization (ISH).

In one embodiment the biolodical sample may be a suspension of cells. Target molecules or structures of cells in suspension may be detected using FC, ELISA, IHC or ISH. When ELISA, IHC or ISH are used for the detection cells of the suspension are to be attached to a solid support, e.g. ELISA plate or ICH slide.

In another embodiment the biological sample may be a slice of a body tissue. Target molecules or structures of cells of such samples will be typically detected using IHC or ISH.

IHC and ISH assay formats usually require a series of treatment steps conducted on a tissue section mounted on a suitable solid support for microscopic inspection, or the production of photomicrographs, e.g., a glass slide or other planar support, to highlight by selective staining certain morphological indicators of disease states or detection of biological markers. Thus, for example in IHC, a sample is taken from an individual, fixed and exposed to antibodies which specifically bind to the biological marker of interest. The sample processing steps may include, for example, antigen retrieval, exposure to a primary antibody, washing, exposure to a secondary antibody (optionally coupled to a HRP moiety), washing, and exposure to a tertiary antibody linked to one or more HRP moieties. Washing steps may be performed with any suitable buffer or solvent, e.g., phosphate-buffered saline (PBS), tris buffered saline (TBS), distilled water. The wash buffer may optionally contain a detergent, e.g., Tween 20.

As mentioned above, there are in general two categories of histological samples: (1) preparations comprising fresh tissues and/or cells, which generally are not fixed with aldehyde-based fixatives, and (2) fixed and embedded tissue specimens, often archived material.

Before performing detection of a target in the IHC assay format, a pre-detection procedure is to be performed. It may involve the steps of: cutting and trimming tissue, fixation, dehydration, paraffin infiltration, cutting in thin sections, mounting onto glass slides, baking, deparaffination, rehydration, antigen retrieval, blocking steps, applying primary antibody, washing, applying secondary antibody—enzyme conjugate and washing.

In ISH, a sample is taken from an individual, fixed and exposed to a nucleic acid binding agent which hybridizes by virtue of complementary base pairing to the nucleic acid of interest. The biological sample typically comprises a detectable nucleic acid, such as DNA and RNA, including messenger RNA. Detection of DNA/RNA levels may indicate the level of expression of a particular gene, and hence may be used to detect a condition (such as a disease condition) of a cell, tissue, organ or organism. The nucleic acid in the sample is typically denatured to expose binding sites. The binding agent is typically a double or single stranded nucleic acid, such as a DNA or RNA, or a nucleic acid analog, such as PNA. The amount of the relevant target protein or nucleic acid detected by such techniques is then assessed to determine whether it is above a certain pre-determined minimum threshold or compared to a known standard, and therefore, diagnostically relevant. Suitable treatment may then be planned for the individual if necessary.

Many methods of fixing and embedding tissue specimens are known, for example, alcohol fixation and formalin-fixation and subsequent paraffin embedding (FFPE).

Fixatives are needed to preserve cells and tissues in a reproducible and life-like manner. To achieve this, tissue blocks, sections, or smears are immersed in a fixative fluid, or in the case of smears, are dried. Fixatives stabilize cells and tissues thereby protecting them from the rigors of processing and staining techniques.

Any suitable fixing agent may be used, for example, ethanol, acetic acid, picric acid, 2-propanol, 3,3'-diaminobenzidine tetrahydrochloride dihydrate, acetoin (mixture of monomer) and dimer, acrolein, crotonaldehyde (cis+trans), formaldehyde, glutaraldehyde, glyoxal, potassium dichromate, potassium permanganate, osmium tetroxide, paraformaldehyde, mercuric chloride, tolylene-2,4-diisocyanate, trichloroacetic acid, tungstic acid. Other examples include formalin (aqueous formaldehyde) and neutral buffered formalin (NBF), glutaraldehyde, acrolein, carbodiimide, imidates, benzoequinone, osmic acid and osmium tetraoxide.

Fresh biopsy specimens, cytological preparations (including touch preparations and blood smears), frozen sections and tissues for immunohistochemical analysis are commonly fixed in organic solvents, including ethanol, acetic acid, methanol and/or acetone.

To facilitate the specific recognition in fixed tissue, it is often necessary to retrieve or unmask the targets, i.e., the biological markers of interest, through pre-treatment of the specimens to increase reactivity of the majority of targets. This procedure is referred to as "antigen retrieval", "target retrieval" or "epitope retrieval", "target unmasking" or "antigen unmasking." An extensive review of antigen retrieval (antigen unmasking) may be found in Shi et al. 1997, *J Histochem Cytochem*, 45(3):327.

Antigen retrieval includes a variety of methods by which the availability of the target for interaction with a specific detection reagent is maximized. The most common techniques are enzymatic digestion with a proteolytic enzyme (for example proteinase, pronase, pepsin, papain, trypsin or neuraminidase) in an appropriate buffer or heat induced epitope retrieval (HIER) using microwave irradiation, heating in a water bath, a steamer, a regular oven, an autoclave or a pressure cooker in an appropriately pH stabilized buffer, usually containing EDTA, EGTA, Tris-HCl, citrate, urea, glycin-HCl or boric acid. Detergents may be added to the HIER buffer to increase the epitope retrieval or added to the dilution media and/or rinsing buffers to lower non-specific binding.

The antigen retrieval buffer is most often aqueous, but may also contain other solvents, including solvents with a boiling point above that of water. This allows for treatment of the tissue at more than 100° C. at normal pressure.

Additionally, the signal-to-noise ratio may be increased by different physical methods, including application of vacuum and ultrasound, or freezing and thawing of the sections before or during incubation of the reagents.

Endogenous biotin binding sites or endogenous enzyme activity (for example phosphatase, catalase or peroxidase) may be removed as a step in the detection procedure, e.g., endogenous biotin and peroxidase activity may be removed by treatment with peroxides. Endogenous phosphatase activity may be removed by treatment with levamisole. Endogenous phosphatases and esterases may be destroyed by heating.

Blocking of non-specific binding sites with inert proteins like, horse serum albumin (HSA), casein, bovine serum albumin (BSA), and ovalbumin, fetal calf serum or other sera, or detergents like Tween20, Triton X-100, Saponin, Brij or Pluronics may be used. Blocking non-specific binding sites in the tissue or cells with unlabeled and target non-specific versions of the specific reagents may also be used.

Samples may also be prepared and target molecules detected using the free floating technique. In this method a tissue section is brought into contact with different reagents and wash buffers in suspension or freely floating in appropriate containers, for example micro centrifuge tubes.

The tissue sections may be transferred from tube to tube with different reagents and buffers during the staining procedure using for example a "fishing hook like" device, a spatula or a glass ring. The different reagents and buffer can also be changed by gentle decantation or vacuum suction. Alternatively, containers with the tissue sections can be emptied into a special staining net, like the Corning "Netwells" (Corning) and the tissue section washed before being transferred back into the tube for the next staining step.

All the steps, including for example fixation, antigen retrieval, washing, incubation with blocking reagents, immuno-specific reagents and the peroxidase-mediated conjugate deposition, are done while the tissue section is floating freely or withheld on nets. After deposition of the conjugate, the tissue section is mounted on slides, the conjugate is detected and slide covered with a cover slip before being analyzed, e.g., by light or fluorescent microscopy.

In some embodiments, the tissue section may be mounted on slides following the critical incubation with the immuno-specific reagents following the procedure (a) of the method. The rest of the process of detection is then conducted on the slide mounted tissue sections.

Detectable by the method, the biological marker may be any molecule or structure present in a sample, preferably in a biological sample, e.g. a protein, glycoprotein, lipoprotein, phosphoprotein, methylated protein, or a protein fragment, e.g., a peptide or a nucleic acid, e.g., DNA, RNA, it a lipid, a glycolipid, or a sugar, a polysaccharide, or a starch. The biological marker may be expressed on the surface of the biological sample, e.g., membrane bound. The marker may be contained in the interior of the biological sample, i.e., within the cell membrane, e.g., within the cytoplasm, within the nucleus, within an intracellular compartment or organelle. The biological marker may be a cellular structure, such as a membrane microdomain, ion channel, chromosomal structure, etc., or it may be a molecular complex, e.g. RNA-protein complex, etc. A biological marker is preferably a specific biological marker, for example it is a marker of a normal or pathological condition, or it is specific for a particular cell or tissue, or specific for a particular biological species. Detection of such biological marker may be useful in diagnosis and treatment of pathological conditions.

The method of the invention may be used for detection of one or more targets in a sample, e.g. one or more biological markers in a biological sample. Accordingly the invention also provides for obtaining data of diagnostic and therapeutic relevance, e.g. information concerning the presence of protein and gene markers of diagnostic relevance. As an example, but not as a limitation, HER2 protein and the HER2 gene can be screened simultaneously in a cancer diagnostic assay, e.g., an assay for breast cancer. Another non-limiting example may include screening for three markers, e.g., to detect cervical cancer. The markers may include Ki67/mib-1, as well as the cellular proliferation marker, p16(INK4a), along with a marker, e.g., a protein or nucleic acid, for human papilloma virus. Yet another non-limiting example includes screening for multiple markers associated with prostate cancer. These markers may include AMACR P504S, high molecular weight cytokeratin (HMW-CK), and p63. Screening this combination of markers provides a method to distinguish benign prostate tumors from malignant ones.

It is desirable to minimize cross-reactivity between binding agents, e.g. where multiple markers are detected. This can be accomplished by e.g. using different binding agents and different conjugate molecules in the detection procedures. A system where two different biological markers are detected may comprise the following steps:

a) performing steps (i) and (ii) using a first binding agent specific for a first biological marker and first conjugate comprising a first detectable label;

b) performing steps (i) and (ii) using a second binding agent specific for a second biological marker and a second conjugate comprising a second detectable label;

c) detecting the deposited first conjugate and thereby detecting the first biological marker;

d) detecting the deposited second conjugate and thereby detecting the second biological marker.

In one embodiment every step of a method of the invention (including every washing step) may be performed the same incubation time, e.g. 30 sec each step, 1 min each step, 2 min each step, 3 min each step, 4 min each step, etc. In another embodiment, time intervals used for performance of each step may vary. All steps of the method (from (i) to (iii) including the washing steps) may be completed within 2-20 min. Such rapid detection may be advantageously used for automated or semi-automated detection of target biological markers. In one embodiment the method is for a manual, automated or semi-automated detection.

Automated staining devices may be used in various embodiments of the invention, for example for the detection of multiple biological markers. Detection of multiple markers frequently requires balancing of the signals derived from the different detectable labels. Automated procedure may include multiple steps of amplification of the signals emanating from target biological markers. It is especially advantageous when multiple markers are to be detected. Automated staining devices are known in the field and the method may be adapted for these devices.

The method may be performed within a wide range of temperatures, e.g. in the interval from +4° C. to +60° C., such as from +10° C. to +40° C., for example at room temperature.

EXAMPLES

1. Conjugates

Abbreviations
MBHA 4-Methylbenzhydrylamine
NMP N-Methyl Pyrolidon
HATU 2-(1 h-7-azabenzotriazole-1-yl)-1,1,3,3 tetramethyl uronium hexafluorophosphate; methenamminium
DIPEA Di/isopropyl EthylAmine
DCM Dichloro Methane
TFA TriFluoroacetic Acid TFMSA TriFluor Methyl Sulphonic Acid
Fer Ferulic acid
Flu Fluorescein
Tyr Tyrosine
Lys Lysine
Dex Dextran
HPLC High Performance Liquid Chromatography
equi. Equivalent
L30 1,10,16,25-tetraaza-4,7,13,19,22,28-hexaoxa-11,15,26,30-tetraoxo-triacontane L60, L90, L120, L150-polymers of the formula $(L30)_q$, wherein q is 2, 3, 4 or 5
ClZ 2-chloroZ=2chloro Benzyloxycarbonyl
FITC FlouresceinIsoThioCyanate
HRP Horse Radish Peroxidase
PNA-X PNA backbone (N-(2-aminoethyl)-glycine) with different substituents coupled to the central nitrogen
A adenine-9-acetic acid,
C cytosine-1-acetic acid,
D 2,6-diaminopurine-9-acetic acid,
G guanuine-9-acetic acid,
Gs 6-thuioguanine-9-acetic acid,
P 2-pyrimidinone-1 acetic acid,
T thymine-1-acetic acid,
Us 2-thiouracil-1-acetic acid.
Dpr 2,3 diamino-propioninc acid,
Caf caffeic acid,
Sin sinapinic acid,
DNP DinitroPhenyl,
Acin 4-amino-cinnamic acid,
Phe phenylalanine,
Tyr tyrosine,
Trp tryptophane,
Lys lysine,
Cys cysteine,
betaala betaalanine, N,N diacetic acid
Conjugates

TABLE 1

Conjugate molecules, intermediate products of their synthesis and control constructs

|   | Conjugate ID | Structure | Synthesis protocol No. |
|---|---|---|---|
| 1 | D19112/D19057 | Fer-Lys(Fer)-Lys(Fer)-L150-Lys(Flu) | 2 |
| 2 | D19185/D20068/D20171/D20166/D21025/D21030/D21032/D21045 | Fer-Lys(Fer)-Lys(Fer)-Lys(Fer)-L150-Lys(Flu) | 2 |
| 3 | D20086 | Fer-Lys(Fer)-Lys(Fer)-L30-Lys(Flu) | 2 |
| 4 | D20118 | Fer-Lys(Fer)-Lys(Fer)-L60-Lys(Flu) | 2 |
| 5 | D20120 | Fer-Lys(Fer)-Lys(Fer)-Glu-L30-Lys(Flu) | 2 |
| 6 | D19048/D21053 | Fer-Lys(Fer)L150-Lys(Lissamine) | 2 |
| 7 | D19059 | Fer-Lys(Fer)-Lys(Fer)-L150-Lys(DNP) | 2 |
| 8 | D18146 | ACin-(Lys(ACin)L30)$_5$-(L90-Lys(Flu))$_3$ | 2 |
| 9 | D18044 | Ac-(Tyr-L30)$_5$-(L90-Lys(Flu))$_3$ | 1 |
| 10 | D21008 | (D18074)$_{18.5}$-Dex70-(D18118)$_{27.7}$ | 8 |
| 11 | D18074/D17120/D17137/D18114 (intermediate) | Fer(Lys(Fer)-L30)$_5$-Lys(NH$_2$) | 3 |
| 12 | D21020 | Caf-Lys(Caf)-Lys(Caf)-L150-Lys(Flu) | 2 |
| 13 | 0328-018/D21047/D21067 | Sin-Lys(Sin)-Lys(Sin)-L150-Lys(Flu) | 2 |
| 14 | D17093 intermediate | Fer(PNA-Fer)5L30-Lys(NH2) | 3 |
| 15 | D17127/D18118 intermediate | NH2-Cys(SH)-L90Lys(Flu)-L90-Lys(Flu)-L90-Lys(Flu) | 1 |
| 16 | D17128 | (D17093)$_{18.6}$-Dex70-(D17127)$_{26.2}$ | 8 |
| 17 | D17130 | (D17120)$_{18.8}$-Dex70-(D17127)$_{18.6}$ | 8 |
| 18 | D17132 control | Dex70-(D17127)$_{23}$ | 7 |
| 19 | D17126/D17165 intermediate | Betaala-L90-Lys(Flu)-L90-Lys(Flu)-L90-Lys(Flu) | 1 |
| 20 | D17134/D17135/D17136 | Fer(Lys(Fer)-L30)5-Lys-(betaala)-(L90-Lys(Flu))3 | 6 |
| 21 | D17138 | Fer(Lys(Fer)-L90)$_5$-Lys(NH$_2$) | 3 |
| 22 | D17139 | Fer-Lys(Fer)L30-(Lys(Fer))2-L30(Lys(Fer))2L30-Lys(NH2) | 3 |
| 23 | D17140 | Fer-Lys(Fer)L60-(Lys(Fer))2-L60(Lys(Fer))2L30-Lys(NH2) | 3 |
| 25 | D17148/D17150/D17151 | Fer-Lys(Fer)-(L30-Lys(Fer)-Lys(Fer))2-L30-Lys-(betaala)-(L90-Lys(Flu))3 | 6 |
| 24 | D17152 | Fer-L30-Lys(L30Fer)-(L30Lys(L30Fer))4-L30-Lys(NH2) | 5 |
| 26 | D17156 | Fer-L30-Lys(L30Fer)-(L30Lys(L30Fer))4-L30-Lys(betaala)-(L90-Lys(Flu))3 | 6 |
| 27 | D17157 | Fer-L150-Lys(Flu) | 2 |
| 28 | D17158 | Fer-L30-Lys(Flu) | 2 |
| 29 | D17161 control | Flu-L150-Lys(Flu) | 1 |
| 30 | D17162 control | Dex270-(D17127)$_{62.9}$ | 7 |
| 31 | D17104 intermediate | Fer-(Lys(Fer)-Gly)4-Lys(Fer)-L30-Lys(NH2) | 3 |
| 32 | D17188 | Fer-(Lys(Fer)-Gly)4-Lys(Fer)-L30-Lys(betaala)-(L90-Lys(Flu))3 | 6 |

TABLE 1-continued

Conjugate molecules, intermediate products of their synthesis and control constructs

| | Conjugate ID | Structure | Synthesis protocol No. |
|---|---|---|---|
| 33 | D17192 intermediate | 7-OH-Cou-(Lys(7-OH-Cou)-L30)5-Lys(NH2) | 3 |
| 34 | D18003 | 7-OH-Cou-(Lys(7-OH-Cou)-L30)5-Lys(betaala)-(L90-Lys(Flu))3 | 6 |
| 35 | D18007 control | Ac-(PNA-D)5-L120-Lys(Flu)-L90-Lys(Flu)-L90-Lys(Flu) | 1 |
| 36 | D18008 control | Ac-(PNA-G)5-L120-Lys(Flu)-L90-Lys(Flu)-L90-Lys(Flu) | 1 |
| 37 | D18009 control | Ac-(PNA-Gs)5-L120-Lys(Flu)-L90-Lys(Flu)-L90-Lys(Flu) | 1 |
| 38 | D18010 control | Ac-(PNA-P)5-L120-Lys(Flu)-L90-Lys(Flu)-L90-Lys(Flu) | 1 |
| 39 | D18011 control | Ac-(PNA-A)5-L120-Lys(Flu)-L90-Lys(Flu)-L90-Lys(Flu) | 1 |
| 40 | D18012 control | Ac-(PNA-C)5-L120-Lys(Flu)-L90-Lys(Flu)-L90-Lys(Flu) | 1 |
| 41 | D18013 control | Ac-(PNA-T)5-L120-Lys(Flu)-L90-Lys(Flu)-L90-Lys(Flu) | 1 |
| 42 | D18014 control | Ac-(PNA-Us)5-L120-Lys(Flu)-L90-Lys(Flu)-L90-Lys(Flu) | 1 |
| 43 | D18015/D18126/D19130 | Fer-(Lys(Fer)-L30)5-(L90-Lys(Flu))3 | 2 |
| 44 | D18019/D18029 intermediate | Fer-(Lys(Fer)-L30)5-L270-Lys(NH2) | 3 |
| 45 | D18031 | (D18019)$_6$-Dex70-(D17127)$_{22.3}$ | 8 |
| 46 | D18049 | Ac-(Tyr)6-L30-(L90Lys(Flu))3 | 1 |
| 47 | D18077 similar to D17130 | (D18074)$_{17.8}$-Dex70-(D17127)$_{22.2}$ | 8 |
| 48 | D18079 similar to D17130 | (D18074)$_{16.8}$-Dex70-(D17127)$_{23}$ | 8 |
| 49 | D18080/19028 intermediate | Fer-(Lys(Fer)-L30)5-(L90-Lys(NH2))3 | 3 |
| 50 | D18081 | Fer-(Lys(Fer)-L30)5-(L90-Lys(Texas-Red-X))3 | 4 |
| 51 | D18084 | NH2-Dpr(NH2)-(L30-Tyr)7 | 1 |
| 52 | D18085 | NH2-Dpr(NH2)-(L90-Lys(Flu))3 | 1 |
| 53 | D18086 control | Dex70(D18085)$_{2.6}$ | 7 |
| 54 | D18088 control | Dex70-(D17127)$_{8.6}$ | 7 |
| 55 | D18090 similar to D17130 | (D18074)$_{16.8}$-Dex70-(D17127)$_{23.9}$ | 8 |
| 56 | D18096 | Fer-(Lys(Fer)-L30)5-(L90-Lys(7-OH-Cou))3 | 4 |
| 57 | D18122 | (D18114)$_{17.6}$-Dex70-(D18118)$_{32.9}$ | 8 |
| 58 | D18128 | NH2-Cys(SH)-(L30-Tyr)5-(L90Lys(Flu))3 | 1 |
| 59 | D18130 | Dex70-(D18128)$_{12.4}$ | 7 |
| 60 | D18132 | NH2-Cys(SH)-(Tyr)5-(L90Lys(Flu))3 | 1 |
| 61 | D18133 | Dex70-(D18132)$_{21.8}$ | 7 |
| 62 | D18137 | Ac-(Tyr)5-(L90Lys(Flu))3 | 1 |
| 63 | D18138 | Ac-(Tyr)5-(L90Lys(DNP))3 | 1 |
| 64 | D18141/D18155/D19032 | Fer-(Lys(Fer)-L30)5-(L90-Lys(DNP))3 | 2 |
| 65 | D18157 | Fer-(L30-Lys(Fer))5-(L90-Lys(Flu))3 | 2 |
| 66 | D19037 | Fer-Lys(Fer)-L150-Lys(Flu) | 2 |
| 67 | D19040/D19046 | Fer-Lys(Fer)-L150-Lys(DNP) | 2 |
| 68 | D21028 | Sin-Lys(Sin)-Lys(Sin)-Lys(Sin)-L150-Lys(Flu) | 2 |
| 69 | D21048 | Sin-Lys(Sin)-Lys(Sin)-L150-Lys(DNP) | 2 |

The different conjugates and intermediates of the table are classified in column 3 according to methods of their synthesis, roughly in increasing order of complexity:
1. Solid phase chemistry only.
2. Solid phase, then one solution phase step.
3. Solid phase, then two solution phase steps.
4. Solid phase, then two solution phase steps
5. Solid phase, then four solution phase steps.
6. Solution phase coupling between amino and betaalaanhydride intermediates.
7. Dextran conjugates with one substituent.
8. Dextran conjugates with two substituents.

1. This group includes the 8 conjugates prepared from Tri Fluorescein labeled PNA-pentamers of the 4 natural and further 4 unnatural bases. (D18007-D18014). There are 4 tyrosin conjugates with 5-6 tyrosines and 3 fluoresceins, D18044, D18049, D18137 and D18138 with three DNPs in place of fluorescein labels. D18128 and D18132 have 5 tyrosines and 3 fluoresceins each, and as such they are potential conjugates, though they also include an N-terminal cystine residue for further dextran coupling, bringing them into the grpoup of "intermediates". Intermediates further include the important Cysteine (D17127) and betaalnine (D17126) tri-fluorescein linkers, as well as the Diaminopropionic-acid linker with 7 tyrosines (D18084) or three fluoresceines (D18085). Finally the small di-fluorescein linker (D17161) used as control was also prepared by solid phase synthesis alone. The synthetic strategy behind all these compound is simple: Boc-protected monomers are commercially available or have prepared in house, and the conjugates and intermediates are prepared by linear solid phase syntheses, followed by cleavage from resin by a cocktail of 6:2:1:1 TFMSA:TFA:m-cresol:thioanisol. For the best results consequent double coupling of all monomers is used. Fluoresceins are introduced on lysine side chains (and the N-terminal, D17161) following Fmoc-deprotection on solid phase. HATU activated Carboxy-fluorescein (mixed isomers) was used for fluorescein labeling (0.2 M in NMP for 3×20 min). DNP labeling was achieved with 2,4-dinitro-fluor-benzene (0.5 M in NMP with DIPEA for 2×10 min).

2. This group includes a large number of conjugates labeled with cinnamic acid derivatives in solution phase following solid phase synthesis of intermediates carrying free N-terminal amino groups and free lysine side chains amino groups. Alpha-N-Boc-(epsilon-N-2-Cl-Z)-lysine was used to introduce lysine residues giving free epsilon-N-amino groups following cleavage from resin. The solution phase labeling is basically an extension of solid phase techniques, utilizing that the relative high molecular weight intermediates can be almost quantitatively precipitated with diethyl ether from TFA or NMP solution.

3. From a synthetic point of view, this group of intermediates represents a yet higher degree of complexity. Solid phase synthesis and solution phase labeling as in 1 and 2, then followed by an additional step of solution phase Fmoc-deprotection. By combining Boc-L30 linkers with Boc-2ClZ and Boc-Fmoc-lysine, intermediates with a combination of protected (Fmoc) lysine side chains and free N-terminal and other lysine side chain free amino groups (from N-terminal Boc and 2-ClZ lysine residues during resin cleavage). These intermediate can be labeled with ferulic acid in solution as in 2. However, prior to the scrubbing step with ethylenediamine, an extra 5 min step with 5% ethanolamine is used. This extra scrubbing step deactivates amino reactive species prior to Fmoc de-protection by ethylenediamine. Without this extra step, ethylenediamine de-protects Fmoc-groups faster than it deactivates HATU activated ferulic acid, and Fmoc "protected" amino groups become labeled with ferulic acid. This group with free amino groups comprises D17120 (six ferulic acids) D17093 (five ferulic acids attached to PNA backbone), D17138 (L90-linkers between ferulic acids) D17139 (six ferulic acids in three close pairs), D17104 (glycine spacers between ferulic acids) D17192 (with six 7-hydroxy coumarins instead of ferulic acids), D18019 (extended L270 linker between closest ferulic acid and free amino group), D18080 (three free amino groups with L90 spacing).

4. From the intermediate D18080 with six ferulic acids and three free aminogroups two conjugates were prepared by further solution phase labeling. D18081 with three Texas-Red-X's and D18096 with three 7-hydroxy coumarins. This illustrates how conjugates can be labeled in solution with two different substituents. The advantage is that the intermediate D18080 can be purified prior to the final labeling, an advantage when using labile or expensive labels such as Texas Red.

5. The synthesis of D17152 illustrates the extent of solid phase synthesis chemistries that can be applied to linkers in solution, followed by repeated precipitation by diethyl ether to remove low molecular weight reactants and solvents: On solid phase NH2-Lys(NH2)-(L30-Lys(NH2))4-L30-Lys(Fmoc) was prepared and cleaved from the resin. Boc-L30 linkers were then coupled to the six free amino groups in solution. The intermediate was precipitated and dissolved in 5% m-cresol in TFA twice. Then ferulic acid labeling was performed as in 2 on the now L30 extended amino groups, followed by ethanolamine and ethylenediamine scrubbing as in 3 and finally 3 TFA precipitations as in 1.

6. Fragment couplings were carried out between amino substituted intermediates and "betaalaanhydride" activated intermediates. D17126 with three fluoresceins further carries an N-terminal betaalanine-N,N-diacetic acid. By activation (NMP:diisopropyl carbodiimide:pyridine; 88:10:2) for 10 min a cyclic "betaalaanhydride" is formed that can be used for coupling to amino groups. This gave D17134 (six ferulic acids with L30 spacing) from D17120, D17148 (six ferulic acids in three pairs with L30 spacing) from D17139, D17156 (six L30 extended ferulic acids) from D17152 and D18003 (with six 7-hydroxy coumarins) from D17192. The advantage of such fragment coupling is that intermediates can be HPLC purified prior to coupling, affording large and complex, yet quite pure conjugates. Another advantage is that a single intermediate as D17126 can be used to prepare a series of related, but different conjugates.

7. Dextran conjugates with a single substituent includes the control fluorescein-only conjugates D17132, D18130 and D18088 (all Dex70 conjugates from D17127 via cystein coupling), D17162 (dex270 conjugate from D17127) and D18086 (from D18085 with less efficient coupling via diamino proprioninc acid). These were used as controls to demonstrate that fluorescein-only conjugates did not work. Conjugates were also prepared this way, by coupling multiple intermediate conjugates to dextran. These include D18133 (dex 70 with L30 spaced tyrosine-fluorescein conjugate D18132) and D18130 (dex 70 with tyrosine-fluorescein conjugate D18128. The advantage of coupling a single conjugate with both HRP substrates and labels, is that a fixed ratio between the two substituents is assured.

8. Dextran conjugates with two different substituents include D17130, D18077, D18079, D18090, D18122 and D21008 that are all dex70 with six ferulic acid linker D18074 and tri-fluorescein linker D17127 (or reproductions of linkers). There was good reproducibility between D17130, D18077, D18079 and D21008 with around 100 ferulic acids and 70 fluoresceins, whereas D18122 was coupled with further excess of fluorescin linker to give a conjugate with approx 100 ferulic acids and fluoresceins each. D17128 resembles D17130, but the ferulic acid linker used (D17093) has ferulic acids attached to PNA backbone rather than lysine side chains. The conjugate D18031 is also with D17127, but with the L270 extended ferulic acid linker D18019. This conjugate was an attempt to make ferulic acids more readily accessible to HRP enzymes.

Examples of Synthesis Procedures for Selected Compounds

D19185: Boc-(Lys(2-Cl-Z))3-L150-Lys(Fmoc) is prepared on solid phase. The Fmoc group is removed, followed by fluorescein labeling as described above. The intermediate NH2-((Lys(NH2))3-L150-Lys(Flu) results from cleavage from resin. It is precipitated with diethyl ether, dissolved in TFA, precipitated then dissolved in NMP and made basic with DIPEA. This solution is mixed with an equal volume of 0.2 M ferulic acid in NMP activated by HATU and DIPEA. After 10 min the labeling is complete and the crude product is further "scrubbed" by addition of ethylene diamine to a concentration of 10% for 5 minutes. Following precipitation with diethyl ether, the product is further dissolved in TFA and precipitated with diethyl ether three times to remove low molecular weight debris. Prior to "scrubbing" with ethylene diamine, mass spectroscopy shows two kinds of adducts (and combinations thereof): +(176)n indicating extra ferulic acids (phenolic esters on other ferulic acids and fluorescein) and +98 (N,N'-tetramethyl uronium adducts, likewise on unprotected phenolic groups). These are completely removed by the ethylene diamine treatment, and active esters and ferulic acid oligomers are likewise decomposed.

The synthesis of D19185 is illustrated in FIG. 1.

The following fluorescein-Ferulic acid conjugates were made according to this scheme: D17157, D17158, D19112, D19185, D18015, D20086, D20118, D20120, D19037 and D18157 (detailed synthesis some of these conjugates is described below). Ferulic acid conjugates with other labels include: D19048 (lissamine labeled); D19059, D18141 and D19040 (DNP labeled). Conjugates with sinnapinic acid in place of ferulic acid were prepared by the same methodology and include 0328-018 and D21028 with fluorescein labels and the DNP labeled D21048. D21020 is with is with three caffeic acids and a fluorescein, D18146 with six 4-amino-cinnamic acids and three fluoresceins and are both prepared by the same strategy.

D17158 MBHA resin was downloaded with Fmoc-Lys (ivDDE) to a loading of 150 micro mol/g. 200 mg resin was de-Fmoc'ed with 20% piperidine in NMP, the subjected to one coupling with Boc-L30-OH (1.5 mL 0.26 M in NMP, preactivated with 0.9 equi. HATU, 2 equivalents DIPEA for 2 min) for 20 min. The ivDDE group was removed with 5% hydrazine in NMP, and the lysine side chain was labelled with carboxy fluorescein (Flu) (1.5 mL 0.2 M in NMP, preactivated for 2 min with 0.9 equi. HATU, 2 equi DIPEA) for 2×20 min. The resin was treated with 20% piperidine in NMP, NMP, DCM then DCM. The intermediate product H-L30-Lys(Flu)-NH$_2$ was cleaved of the resin with TFA:TFMSA:mCresol (7:2:1, 1.5 ml for 1 h), precipitated with diethyl ether, re-suspended in TFA, precipitated with diethyl ether, re-suspended in NMP and again precipitated with diethyl ether. It was made basic with 100 microL DIPEA and dissolved directly in 0.5 mL 0.3M Ferulic acid preactivated with 0.9 equi. HATU and 2 equi. DIPEA. After 25 min the crude product was precipitated with diethyl ether, dissolved in 450 microL NMP and 50 microL ethylenediamine. After 5 min the product was precipitated with diethyl ether, dissolved in 15% acetonitril in water (8 mL) and acidified with 100 microL TFA and subjected to RP-HPLC purification.

D17157 MBHA resin was downloaded with Boc-Lys (Fmoc) to a loading of 100 micro mol/g. 100 mg resin was subjected to 5 coupling cycles with Boc-L30-OH (a. Coupling with Boc-L30-OH as in 1. b. Capping with 2% acetic anhydride in NMP:Pyridine 1:1, 2 min. c. De-Bc with 5% mCresole in TFA 2×5 Min.). The lysine side chain was De-Fmoc'ed and labelled with carboxy fluoresceine, as in 1. The intermediate product H-L150-Lys(Flu)-NH$_2$ was cleaved of the resin, and labelled N-terminally with Ferulic Acid and purified as in 1.1.

D16127 Boc-L90-Lys(Fmoc)-L90-Lys(Fmoc)-L90Lys (Fmoc) was prepared on 0.5 g MBHA resin with standard solid phase chemistry (as in 1.1. and 1.2). Fmoc groups were removed from lysine side chains with 20% piperidine in NMP and the compound was subjected to repeated carboxy fluorescein labelling (3×30 min). Following removal Boc groups with TFA, the N-terminal was labeled on solid phase with betaalanine-N,N-di acetic acid (betaala) tert-butyl ester. Following cleavage from resin and HPLC purification, betaala-L90-Lys(Flu)-L90Lys(Flu)-L90-Lys(Flu)-NH$_2$ was isolated.

D17127 Boc-L90-Lys(Fmoc)-L90-Lys(Fmoc)-L90Lys (Fmoc) resin was prepared and labeled with fluorescein using the procedure described in 1.3. Following removal Boc groups the N-terminal was labeled with N-Boc-S(4-Methoxybenzyl)-Cys-OH. The compound was cleaved from the column and purified by HPLC:

D18074/D17128 To MBHA resin was sequentially coupled Boc-Lys(Fmoc) (2 cycles), Boc-L30-OH (5 cycles) and Boc-Lys(2ClZ)-OH. The intermediate product was cleaved from the resin in the presence of 10% thioanisol scavenger to remove 2ClZ-groups. The N-terminal and the 5 de-protected lysine side chains were labeled with Ferulic acid as in 1.1 (2×30 Min). The Fmoc group on the N of the C-terminal Lysine residues was then removed with 10% ethylene diamine in NMP prior to purification.

D17134 betaala-L90-Lys(Flu)-L90Lys(Flu)-L90-Lys (Flu)-NH2 (D16126) (see 1.4 above) 500 nmol was dissolved in 88 microL NMP and 2 microL pyridine, and converted to cyclic anhydride by reaction with 10 microL diisopropyl carbodiimide for 10 min. The anhydride was precipitated with diethyl ether, and the pellet was dissolved in 100 microL NMP comprising 250 nmol Fer-(Fer-L30)$_5$-Lys(NH$_2$)—NH$_2$. After 20 min 5 microL ethylene diamine was added, and after 5 min the product was precipitated with diethyl ether, acidified and HPLC purified.

D18044 Ac-(Tyr(2BrZ)-L30)$_6$-L90-Lys(Fmoc)-L90-Lys (Fmoc)-Lys(Fmoc) was prepared on MBHA resin. On solid phase the Fmoc groups were removed, and the lysine side chains labeled with carboxy fluorescein. Following cleavage from the resin, the product was HPLC purified.

D17140 Boc-Lys(2ClZ)-L60-Lys(2ClZ)-Lys(2ClZ)-L60-Lys(2ClZ)-Lys(2ClZ)-L30-Lys(Fmoc) was prepared on MBHA resin. Following cleavage from the resin, the intermediate product H-Lys(NH$_2$)-L60-Lys(NH$_2$)-Lys(NH$_2$)-L60-Lys(NH$_2$)-Lys(NH$_2$)-L30-Lys(Fmoc) was isolated by precipitation, and labeled with Ferulic acid as in 1.1. The final product was isolated by HPLC.

D18090 Dextran MW 70 kDa, activated with divinyl sulphone, 10 nmol, was reacted with Fer-(Fer-L30)$_5$-Lys (NH$_2$)—NH$_2$ (D18074) (see (see 1.4 above). 500 nmol, in a total volume of 300 microL 0.16M NaHCO$_3$ pH 9.5 for 30 min at 40 C. After a slight precipitation was observed, further 100 microL water was added and the reaction was allowed to proceed for another 30 min. Further 200 microL 0.15 M NaHCO$_3$ was added together with 500 nmol H-Cys-L90-Lys(Flu)-L90Lys(Flu)-L90-Lys(Flu)-NH2 (D17127) (see 1.5 above). After 1 h at 40 C, the reaction mixture was quenched by addition of 50 microL 0.165M cystein for 30 min, solution was filtered, and the product was purified by FPLC on superdex 200 with 20% EtOH in aqueous solution containing 10 mM CHES, pH 9.0, and 0.1 M NaCl. The product eluted was a Dextran conjugate comprising around 56 Fluorescein and 113 Ferulic Acid residues.

D19112 On solid phase MBHA resin Boc-Lys(2Clz)-Lys (2ClZ)-L150-Lys(Fmoc) was prepared using standard solid phase Boc chemistry. The Fmoc group was removed using 20% piperidine in NMP (2×5 min), and the free amino group was labeled with carboxy fluorescein (0.2 M carboxy fluorescein activated with 0.9 equi.HATU and 1 equi. DIPEA in NMP for 3 times 20 min). The resin was then subjected to treatment with 20% piperidine in NMP for 2×5 min. Cleavage from the resin was performed in TFA:TFMSA:m-cresole:thioanisole (6:2:1:1) mixture for one hour and resulted in the intermediate product H2N-Lys(NH2)-Lys(NH2)-L150-Lys(Flu). This product was dissolved in TFA, precipitated with diethyl ether, and then dissolved in NMP and again precipitated with diethyl ether. The precipitate was then dissolved in 0.3 M ferulic acid activated with 0.9 equivalents HATU and two equivalents Diisopropyl-ethyl-amine. After 10 min reaction, the product was precipitated with diethyl ether and then dissolved in 10% ethylenediamine in NMP for 2 min. The final product was then precipitated with diethyl ether, dissolved in 30% acetonitrile in water and HPLC purified on a C18 column.

D19185, D20068 and D20171 were prepared in the same way as D19112, with the introduction of an additional Lys(Fer) group.

D21020: Caf-Lys(Caf)-Lys(Caf)-L150-Lys(Flu), was prepared as D19185. Following solid phase synthesis, caffeic acid labeling was performed in solution.

0328-018: Sin-Lys(Sin)-Lys(Sin)-L150-Lys(Flu) was prepared as D19185. Following solid phase synthesis, sinapinnic acid labeling was performed in solution D20118: was prepared in the same way as D19112, using L60 linker.

D20086: was prepared in the same way as D19112, using L30 linker.

D20120: was prepared in the same way as D19112, using L30 linker, and, additionally, a glutamic acid residue. Boc-Glu(O-benzyl) was used for solid phase synthesis to build in the glutamic acid residue.

D19048: On 0.5 g MBHA resin Boc-$L_{150}$-Lys(Fmoc) was prepared. The Fmoc group was removed and the lysine side chain amino group was labeled with Lissamin (Molecular Probes product nr. L20, rhodamine B sulphonyl chloride) using 100 mg in 2 mL NMP with addition of 80 microL DIPEA for 3 times 10 min. The Boc group was then removed with TFA, and Boc-Lys(2ClZ) was coupled to the N terminal. The intermediate product $H_2N$-Lys($NH_2$)-L150-Lys (Lissamine) was cleaved from the resin with TFA:TFMSA: m-cresole:thioanisole (6:2:1:1) and labeled with ferulic acid as described for D19112 to give Fer-Lys(Fer)-L150-Lys (Lissamin). The product was purified by RP-HPLC, splitting into two separate peaks representing different isomers of Lissamine. The first isomer turned almost colorless in basic aqueous solution, and was discharged. The second isomer retained color and fluorescence in basic aqueous solution and was collected.

D19059: was prepared in the same way as D19112, but labeled on the C-terminal lysine side chain amino group on solid phase with DiNitroPhenyl using 100 mg 2,4-dinitrofluorobenzen in 1.5 mL NMP with addition of 50 microL DIPEA for 2 times 20 min.

D18126: Fer-Lys(Fer)-L30-Lys(Fer)-L30-Lys(Fer)-L30-Lys(Fer)-L30-Lys(Fer)-L120-Lys(Flu)-L90-Lys(Flu)-L90-Lys(Flu)=Fer-(Lys(Fer)-L30)5-(L90-Lys(Flu))3. This extended conjugate was prepared by the same route as D19112: Boc-(Lys(2ClZ)-L30)5-(L90-Lys(Fmoc))3 was prepared on solid phase. The three Fmoc groups were removed with piperidine in NMP, and three carboxy fluoresceins introduced as in D19112. The intermediate product, NH2-(Lys(NH2)-L30)5-(L90-Lys(Flu))3 was cleaved of the resin and labeled with Ferulic acid at the N-terminal and 5 free lysine side chains, washed with 10% ethylenediamine in NMP, precipitated from TFA and HPLC purified.

D18146: ACim-(Lys(ACim)L30)5-(L90-Lys(Flu))3 was prepared on the same Lysine-Linker skeleton as D18126. Following cleavage from solid phase, the intermediate fluorescein labeled linker was dissolved in NMP and made basic with DIPEA. 4-amino-cinnamic acid, 0.1 M in NMP was activated with 0.9 equi.HATU and 3 equi DIPEA for 30 seconds, and added to the linker. The reaction was quenched after 2 min by addition of ethylenediamine to a final concentration of 10%. Following precipitation the product was purified by RP-HPLC.

D18074: Fer(Lys(Fer)-L30)5-Lys(NH2). this intermediate linker with 6 ferulic acids and a free lysine side chain amino group was prepared by solid phase chemistry, using a C terminal Boc-Lys(Fmoc) followed by alternating coupling with Boc-L30 linker and Boc-Lys(2ClZ). Following cleavage from resin, the intermediate product NH2(Lys (NH2)-L30)5-Lys(Fmoc) was labeled with ferulic acid in solution as described for D19112. In the final treatment with 10% ethylenediamine, the Fmoc group was also removed. This homo ferulic acid oligomer was used in the preparation of dextran conjugate D21008.

D18118: NH2-Cys-(L90Lys(Flu)) This intermediate trifluorescein linker was prepared directly on solid phase, using Boc-Lys(Fmoc) to introduce lysines, that following removal of the Fmoc were labeled with carboxy fluorescein. The N-termina cystein was introduced using Boc(S-p-methoxybenzyl) cysteine.

D18044: On solid phase Fer-(Tyr-L30)5-(L90-Lys(Flu))3 was prepared as D18126. N-Boc-O-2BrZ tyrosine was used to introduce the tyrosines. Following cleavage from the resin the product was HPLC purified.

D21008: Dex70 conjugate with D18074 and D18118. 10 nmol vinyl sulphone activated 70 kDa dextran in 140 microL water was mixed with further 200 microL water and 60 microL 0.8 M sodium hydrogen carbonate, pH 9.5. This mixture was used to dissolve 500 nmol freeze dried D18074. The reaction mixture was maintained at 40 C for 60 min, then further 500 mmol D18118 dissolved in 250 microL water was added to the reaction mixture together with further 50 microL 0.8M sodium hydrogen carbonate, pH 9.5. After additional 60 min reaction at 40 C, the reaction was stopped by addition of 70 microL 0.165 mM cystein in 0.8 M sodium hydrogen carbonate, pH 9.5. The conjugate was purified on superdex 200, using 10 mM CHES pH 9.0, 100 mM NaCl in 20% ethanol in water as eluent. This resulted in a first peak containing the conjugate, followed by unconjugated linkers. Based on a total recovery of 81% of fluorescien and ferulic acid, and assuming the same recovery rate (81%) for the dextran conjugate, a ratio of 111 ferulic acids and 83 fluoresceins per dextran was calculated, corresponding to $(D18074)_{18.5}$-Dex70-$(D18118)_{27.7}$.

D19059: On 0.1 g of MBHA resin with standard solid phase chemistry Boc-Lys(2ClZ)-Lys(2ClZ)-$L_{150}$-Lys (Fmoc) was prepared. The Fmoc protected Lysine side chain was deprotected with 20% piperidine in NMP (2×5 min) and subjected to labeling with 150 mg 2-4-dinitro-fluorobenzene dissolved in 1.5 ml NMP 1.5 mL and 50 μL DIPEA for 2×20 min. The resin was treated with 20% piperidine in NMP, NMP and DCM.

The intermediate product was cleaved of the resin with TFA:TFMSA:thioanisol:m-cresol (6:2:1:1, 1.5 mL, for 1 h), precipitated with diethyl ether, resuspended in TFA, precipitated with diethyl ether, resuspended in NMP and again precipitated with diethyl ether. It was made basic with 100 μL DIPEA and dissolved directly in 0.5 mL 0.3 M Ferulic acid preactivated with 0.9 equi HATU and 2 equi DIPEA. After 10 min. the crude product was precipitated with diethyl ether, redissolved in 900 μL NMP and 100 μL ethylendiamine. After 2 min. the product was precipitated with diethyl ether. Resuspended in TFA, precipitated with diethyl ether, dissolved in 22% acetonitril in water (8.2 mL) and subjected to RP-HPLC purification.

Yield 8 μmol, MS found 3582 (M+Na), calc 3558,784 for Fer-Lys(Fer)-Lys(Fer)-$L_{150}$-Lys (DNP)

D19112: On 1 g of MBHA resin with standard solid phase chemistry Boc-Lys(2ClZ)-Lys(2ClZ)-$L_{150}$-Lys(Fmoc) was prepared. The Fmoc protected Lysine side chain was deprotected with 20% piperidine in NMP (2×5 min) and subjected to repeated carboxy fluorescein labeling (3 mL 0.2 M in NMP, preactivated for 2 min with 0.9 equi HATU, 1 equi DIPEA) 3×20 min. The resin was treated with 20% piperidine in NMP then washed with NMP, DCM and TFA. The intermediate product was cleaved of the resin with TFA:TFMSA:thioanisol:m-cresol (6:2:1:1, 3 mL, for 1 h), precipitated with diethyl ether, resuspended in TFA, precipitated with diethyl ether, resuspended in NMP and again precipitated with diethyl ether. It was made basic with 200 μL DIPEA and dissolved directly in 2 mL 0.3 M Ferulic acid preactivated with 0.9 equi HATU and 2 equi DIPEA. After 10 min. the crude product was precipitated with diethyl ether, redissolved in 1350 μL NMP and 150 μL ethylendiamine was added. After 2 min. the product was precipitated with diethyl ether. Resuspended in TFA, precipitated with diethyl ether, dissolved in 25% acetonitril in water (24 mL) and subjected to RP-HPLC purification.

Yield 19 μmol, MS found 3749, calc 3750,998 for Fer-Lys(Fer)-Lys(Fer)-$L_{150}$-Lys (Flu)

D19185: D19185 was prepared analogously to D19112, by solid phase synthesis, followed by labelling with Ferulic acid in solution. MS found 4054

D19037: D19037 was prepared analogously to D19112, by solid phase synthesis, followed by labelling with Ferulic acid in solution. MS found 3447

D18126: On MBHA resin with standard solid phase chemistry Boc-(Lys(2ClZ)-$L_{30}$)$_5$$L_{90}$-Lys(Fmoc)-$L_{90}$Lys (Fmoc)-$L_{90}$ Lys(Fmoc)) was prepared. The Fmoc protected Lysine side chain was deprotected with 20% piperidine in NMP (2×5 min) and subjected to repeated carboxy fluorescein labeling (3 mL 0.2 M in NMP, preactivated for 2 min with 0.9 equi HATU, 1 equi DIPEA) 3×20 min. The resin was treated with 20% piperidine in NMP then washed with NMP, DCM and TFA. The intermediate product was cleaved of the resin with TFA:TFMSA:thioanisol:m-cresol (6:2:1:1, 3 mL, for 1 h), precipitated with diethyl ether, resuspended in TFA, precipitated with diethyl ether, resuspended in NMP and again precipitated with diethyl ether. It was made basic with 200 μL DIPEA and dissolved directly in 2 mL 0.3 M Ferulic acid preactivated with 0.9 equi HATU and 2 equi DIPEA. After 10 min. the crude product was precipitated with diethyl ether, redissolved in 1350 μL NMP and 150 μL ethylendiamine was added. After 2 min. the product was precipitated with diethyl ether. Resuspended in TFA, precipitated with diethyl ether, dissolved in 25% acetonitril in water (24 mL) and subjected to RP-HPLC purification.

Yield 2 μmol, MS found 10666,

1. Biding Agents

Goat-Anti-Mouse-Dex70-HRP (D18033/D18175)

13.7 nmol divinylsulphone were activated 70 kDA MW dextran and reacted with 602 nmol HRP were in 600 microL buffer (100 mM NaCl, 25 mM NaHCO$_3$, pH 9.5) for 3 h at 30 C. Then 41.1 nmol Goat-anti-Mouse F(ab)$_2$ antibody in 105 microL water was added, and the reaction was continued for additional 16 h. The reaction mixture was quenched by addition of 70 microL 0.165M cystein for 30 min and the product was purified on superdex 200 in 100 mM NaCl, 10 mM HEPES pH 7.2. The eluded product was a Dextran conjugate comprising Goat-anti-Mouse (GaM) and HRP (Ratio dex:GaM:HRP=1:1.1:7.5).

Anti-FITC-Dex70-HRP (D18058/D18144)

10 nmol divinylsulphone activated 70 kDA MW dextran and 440 nmol HRP were reacted in 400 microL buffer (100 mM NaCl, 25 mM NaHCO$_3$, pH 9.5) for 3 h at 30 C. Then, 30 nmol Anti-Mouse F(ab)$_2$ antibody in 80 microL water was added and the reaction was continued for additional 90 min at 40 C. The reaction mixture was quenched by addition of 50 microL 0.165M cystein for 30 min and the product was purified on superdex 200 in 100 mM NaCl, 10 mM HEPES pH 7.2. The eluded product was a conjugate of Dextran with anti-FITC and HRP (Dex/anti-FITC/HRP Ratio=1/2/9).

Anti-FITC-Dex70-HRP (D17030)

10 nmol divinylsulphone activated 70 kDA MW dextran; 440 nmol HRP and 25 nmol F(ab)$_2$ anti-FITC were reacted in 374 microL buffer (100 mM NaCl, 25 mM NaHCO$_3$, pH 9.5) for 16 at 30 C. The reaction mixture was quenched by addition of 50 microL 0.165M cystein for 30 min and the product purified on superdex 200 in 100 mM NaCl, 10 mM HEPES pH 7.2. The eluded product was a Dextran conjugate comprising Anti-FITC and HRP (ratio 1:1:1).

Rabbit-Anti-FITC F ab')$_1$-HRP Conjugate (D19142)

Polyclonal rabbit-anti_FITC IgG antibody was digested with pepsin for 4 h at 37 C. and subjected to purification on superdex 200 to remove pepsin and Fc fragments.

The F(ab')$_2$ fragment was further dialysed against 5 mM EDTA in 0.2 M sodium phosphate, pH 6.0. The solution was concentrated with Amicon Ultra spin columns to a protein concentration of 25 g/L. To 6.0 mL of said solution (150 mg F(ab')$_2$) was added 487 microL 50 mg/mL DTT and 423 microL 56 mM 2-mercaptoethanol, both in water. The reaction mixture was gently stirred for 40 min at room temperature, and immediately after purified on PD-10 column with 5 mM EDTA in 0.2 M sodium phosphate, pH 6.0. 118 mg F(ab')$_1$ was recovered in 8.0 mL buffer.

HRP (Servac), 250 mg, was dissolved in 2.5 mL 0.15 m NaCL, 0.05M potassium phosphate pH 8 and dialysed against the same buffer. Following dialysis the enzyme solution was concentrated and adjusted to a concentration of 40 mg/mL. To 3.21 mL, 128.6 mg HRP solution was added 860 micoL 15 mg/mL SMCC, and the reaction was allowed to proceed for 30 min in the dark at room temperature. The SMCC activated HRP enzyme was purified on PD-10 column with 0.15 m NaCL, 0.05M potassium phosphate pH 8. 126.9 mg were recovered in 7.9 mL.

To the 8.0 mL of F(ab')$_1$ was added 6.25 mL of the SMCC activated HRP solution, and the total volume was adjusted to 43.8 mL with 0.15 m NaCL, 0.05M potassium phosphate pH 8. The reaction between antibody fragment and enzyme was carried out for 210 min in the dark at room temperature. The reaction was then quenched by addition of 343 microL 25 mg/mL cysteamine in water for 15 min at room temperature, and the reaction mixture was stored in the cold over night awaiting purification. The sample was concentrated to 8 mL, and in 4 portions applied to a superdex 200 column and eluded with 150 mM NaCL, 50 mM Tris, pH 7.6. The product eluded in the first peak, followed by a peak of un-reacted antibody and enzyme. 100 mg of conjugate was isolated in several fractions. UV-measurements at 280 nm/403 nm showed antibody enzyme ration between 0.8 and 1.2.

Goat-Anti-Mouse F(ab')$_1$-HRP (D19150)

Goat-anti-Mouse F(ab')$_1$-HRP was prepared as Rabbit-anti-FITC F(ab')$_1$-HRP, by reduction of F(ab')$_2$ with DTT and mercaptoethanol and coupling to SMCC activated HRP. As with Rabbit-anti-FITC F(ab')$_1$-HRP, 12 equivalents of SMCC was used for HRP activation and a 1:1 molar ration between F(ab')$_1$ and HRP was used.

Goat-Anti-Rabbit F(ab')$_1$-HRP AMM 279.168

Goat-anti-Rabbit F(ab')$_1$-HRP was prepared as Rabbit-anti-FITC F(ab')$_1$-HRP, by reduction of F(ab')$_2$ with DTT and mercaptoethanol and coupling to SMCC activated HRP. As with Rabbit-anti-FITC F(ab')$_1$-HRP, 12 equivalents of SMCC was used for HRP activation and a 1:1 molar ration between F(ab')$_1$ and HRP was used.

2. IHC Staining by the Method of the Invention

IHC was carried out on samples of formalin fixed paraffin embedded tissue loaded on glass slides. 3-5 micron tissue sections were cut, baked and stored at 4 C, until used. Paraffin was then removed by xylene (2×5 min); 99% ethanol (2×2 min); 70% ethanol (2×2 min) and finally water. The slides were put in the target retrieval solution, pH 9, (DAKO S2367) then heated in microwave oven (boiled for 10 min). Afterwards, the slides were allowed to cool and then were transferred to the wash buffer (DAKO S3006). The procedure was followed by a step of blocking of endogenous Peroxidase activity with 3% hydrogen peroxide for 5 min, then again the slides were transferred into the wash buffer and then stained under varying conditions. The staining procedures and their results are in detail described below (Experiments 1-10). To minimize slide to slide variation each comparative experiment was carried out with consecutively cut sections during the same day. The specific as well as background signals were scored using a score scale from 0 to 4 wherein 0 is representing no stain at all, 1-weakly stained, 2-moderately stained, 3-strongly stained, 4-over stained. As comparative "standard" staining to evaluate the results of staining procedures of the invention the reference Envision Flex (DAKO K8010) stains were performed according to the manufacturer's recommendations, briefly: slides were sequentially incubated with 2. Primary antibody diluted in S0809 (DAKO) (see Antibody Table below), 20 min;
3. Envision Flex HRP (DAKO DM807), 20 min, or EnvisionFlex mouse linker (DAKO DM804) 15 min (only antibodies with "link" in table 1))
4. Envision Flex DAB chromogen (DAKO DM807) diluted 1:50 in DM803 (DAKO), 2×5 min

TABLE 2

Antibody

| Antibody | DAKO catalog reference | Dilution |
|---|---|---|
| Human Ki67, clone MIB1 | M7240 | 1:100 |
| Estrogen receptor, clone 1D5 | M7047 | 1:35 |
| BCL6 protein, clone PG-B6p | M7211 | 1:75 (link) |
| CD20cy, clone L26 | M0755 | 1:200 |
| CD5, cloneCD5754/F6 | M7194 | 1:50 |
| Carcinoembryonic Antigen, clone II-7 | M7072 | 1:200 |
| ProstataSpesificAntigem, cloneER-PR8 | M0750 | 1:100 |
| Cytokeratin Clone AE1/AE3 | M3515 | 1:50 |
| Cytokeratin 5/6 clone D5/16 B4 | M7237 | 1:40 |
| Synaptophysin, clone Sy38 | M0776 | 1:50 |
| CD31, Endothelial cell, clone JC70A | M0823 | 1:100 (link) |
| CD68, clone PG-M1 | M0876 | 1:100 |
| Smooth muscle Actin, clone 1A4 | M0851 | 1:165 |
| CD21, clone 1F8 | M0784 | 1:50 (link) |
| Neurofilament protein, clone 2F11 | M0762 | 1:400 |

All conjugates and control compounds of table 1 have been tested at least one using a procedure of Experiment 1 some of the conjugates also using the procedures of other below described experiments. There were no staining observed in slides processed with compounds identified as "control". All other compounds (excluding marked "intermediate" which are intermediate constructs in synthesis of large conjugates) showed target labeling with an intensity grading from +1 to +4. The experiments below describe different embodiments of IHC procedures perfomed with selected conjugates of the table 1.

Experiment 1

Slides were sequentially incubated:
1. Primary antibody 80 seconds. (300 seconds for "Link" antibodies)
2. Goat-anti-Mouse F(ab')-HRP, 20 nM, 80 seconds
3. Conjugate D19185 1200 nM+5.6 mM DAB 200 seconds
4. Anti-FITC F(ab')-HRP, 100 nM, 140 seconds 5. 5.6 mM DAB 200 seconds.

Primary antibodies were diluted in antibody diluent S0809 (DAKO) as indicated in the Antibody Table (above).

Goat-anti-Mouse-HRP and anti-FITC-HRP were diluted in buffer with 0.4% casein, 2% BSA, 2% PEG 3000, 0.1% procline, 0.05% 4-aminoantipyrine, 0.1% Tween-20, 100 mM NaCl, 10 mM Tris pH 8.0 (ABCPT buffer).

Conjugate D19185 ($Fer_4$-$L30_5$-$Flu_1$) and DAB of step 3, and DAB of step 5 were diluted in water solution of 50 mM imidazol-HCl pH 7.4, 5.6 mM hydrogen peroxide, 0.1% Tween-20

Washings between the steps were performed in S0809 (in S0809 or 10 mM CHES pH 9, 0.1% Tween-20 after step 3), each 2 min at room temperature.

The procedure was tested using 15 different antibodies of the table on 12 different human tissues: tonsil, liver, mamma carcinoma, carcinoid, colon cancer, melanoma, prostate, cerebellum, kidney, pancreas. The overall intensity of tissue stains by the procedure of the invention and Envision Flex procedure performed on the corresponding tissues was the same; the hue as well as staining intensity of high and low expression targets (High/Low balance) was also identical, however, the staining by the present procedure appeared to be more crisp (i.e. more sharp and clear). In some tissues containing small cellular structures, e.g. colon carcinoma, cytoplasmatic staining was slightly less crisp when the present procedure was used. Slides treated with antibody diluent alone, i.e. without antibody, demonstrated no staining, i.e. the stains by both procedures were specific.

The experiment shows that using the same antibody at same dilutions but significantly shorter incubation times (i.e. 15 times shorter), the procedure of the invention the staining results in staining of the same pattern and quality as Envision Flex straining.

Experiment 2

Slides were sequentially incubated:
1. Primary antibody, 140 seconds. (300 seconds for "Link" antibodies")
2. Goat-anti-Mouse F(ab')-HRP (D19150), 30 nM, 200 seconds
3. Conjugate D19059 1200 nM+2.8 mM DAB 200 seconds
4. Anti-FITC F(ab')-HRP (D19142), 150 nM, 140 seconds
5. 2.8 mM DAB 200 seconds.

Primary antibodies were diluted in antibody diluent, S0809 (DAKO) 10 times more (5 times more for "Link" antibodies) than indicated in the Antibody Table above.

Solvents for secondary antibody, conjugate and DAB, and washing buffer were as in experiment 1.

The procedure was tested with the same 15 different antibodies on same 12 different human tissues (above) using incubation time that is about 9 times shorter than incubation time of the Envision Flex. Both staining pattern and quality were essentially identical to the staining of experiment 1. There was no background on control slides treated with antibody diluent alone in step 1.

The experiment shows that sensitivity of detection of specific targets by the procedure according to the invention is at least 10 times higher than by the Envision Flex procedure (the Envision Flex procedure was performed as in experiment 1, i.e. without any modification). This experiment also shows that a reduced concentration of DAB in the deposition solution of step 2 and staining solution of step 5 (2.8 mM instead of 5.6 mM) does not affect the staining results.

Experiment 3

Slides were sequentially incubated:
1. Anti-Cytokeratin (clone AE1/A3, Dako Catalog No. M3515) diluted 45 times more, than indicated in the Antibody table, 20 min.
2. Goat-anti-Mouse F(ab')-HRP (D19150), 30 nM, 5 min.
3. Conjugate D19185 1200 nM+2.8 mM DAB 200 seconds
4. Anti-FITC F(ab')-HRP (D19142), 150 nM, 140 seconds
5. 2.8 mM DAB 200 seconds.

The primary antibodies were diluted in antibody diluent S0809 (DAKO) 45 times more (5 times more for "Link" antibodies) than indicated in the table (above). Solvents for secondary antibody, conjugate and DAB, and washing buffer were as in experiment 1.

The obtained stain was essentially identical to the Envision Flex stain with anti-Cytokeratin in 45× higher concentration (using the same incubation time). There was no background on control slides treated with S0809 (without antibody) in step 1.

The experiment shows that a 45 times extra dilution of the antibody (compared to the recommended in the table above) is optimal with regard to intensity of staining, i.e. the sensitivity of the current procedure is at least 45 times higher than sensitivity of Envision Flex procedure. This experiment also confirms that a reduced concentration of DAB in the deposition solution of step 2 and staining solution of step 5 (2.8 mM instead of 5.6 mM) does not affect the staining results.

Experiment 4

Slides were sequentially incubated:
1. Anti-Cytokeratin (clone AE1/A3, Dako Catalog No. M3515) diluted 1000 times more than recommended (see the table above), 20 min.
2. Goat-anti-Mouse F(ab')-HRP (D19150), 30 nM, 5 min.
3. Conjugate D19185 1200 nM+(1.4 to 2.8 mM DAB) 200 seconds
4. Anti-FITC F(ab')-HRP (D19142), 150 nM, 140 seconds
5. 2.8 mM DAB 5 min.
6. 2.8 mM DAB 5 min.

Solvents for secondary antibody, conjugate and DAB, and washing buffer were as in experiment 1.

The intensity of the stain with 2.8 mM DAB in the deposition buffer of step 3 was much weaker than the Envision Flex staining. However the target highly expressed in tonsil and colon epithelium, mamma carcinoma cytoplasm, hepatic bile ducts and renal cells was still moderately (+2) stained with this protocol. A decrease of the concentration of DAB in the deposition solution in step 3 from 2.8 mM to 1.4 mM significantly increased the intensity of the stain but at the cost of reduced crispness. High expression samples were strongly stained (+3) and most of medium expression samples were moderately stained (+2). Low expression tissues were however weakly stained or not stained at all (0 to +1).

At 2.8 mM DAB in step 3 there was no background on control slides treated with buffer without antibody in step 1, but with the increased level of amplification associated with 1.4 mM DAB in step 4, led to some background staining emerged on control slides treated with S0809 in step 1.

Further control experiments where the goat-anti-mouse-HRP was omitted from the treating solution in step 2 showed that the background was associated primarily from this conjugate, not the subsequent steps, i.e. deposition of the conjugate in the presence of DAD and final DAB staining.

The experiment shows that the signal amplification system of the present procedure is so strong that it allows diluting an antibody reagent up to 1000 more than recommended and still remain the quality of the stain.

Experiment 5

Slides were sequentially incubated
1. Primary antibody (dilution according the table), 80 seconds. (300 seconds for "Link" antibodies)
2. Goat-anti-Mouse F(ab')-HRP (D19150), 50 nM, 140 seconds
3. Conjugate D19185 1000 nM+5.8 mM DAB, 80 seconds
4. Anti-FITC F(ab')-HRP (D19142), 150 nM, 140 seconds
5. 5.6 mM DAB 80 seconds.

Both conjugate D19185+DAB of step 3 and DAB of step 5 were diluted in water solution of 50 mM imidazol-HCl pH 7.4, 56 mM $H_2O_2$, 0.1% Tween (i.e. the concentration of $H_2O_2$ was 10 times higher compared to experiments 1-4)

The procedure was carried out with 15 different antibodies on 12 different human tissues (as experiment 1).

The results of staining were similar to Envision Flex stains with regard to intensity, though low expression targets were slightly less intense. There was no background on control slides treated without antibody in step 1. The hue was slightly different: generally grey to black rather than light to dark brown of Envision FLEX. Control experiments with increased time (200 seconds), reduced DAB (2.8 mM) and reduced hydrogen peroxide (5.8 mM) in step 5 resulted in a typical brown hue, showing that the hue is predominantly determined by final (staining) step.

This protocol produced a staining of great crispness: small cellular structures in colon and colon carcinoma samples were seen as very distinct and clear; membrane stains were sharp; areas with intensely stained cytoplasm sharply confined contrasting very clear blue nuclei; moderately stained nuclei showed fine intra nuclear details invisible with homogeneous stain produced by Envision FLEX.

Manual control experiments with reduced incubation time in step 3 and 5 showed that the intensity of the stains does not increase by extending the incubation time beyond 30 seconds in these steps when the concentration of hydrogen peroxide high (56 mM).

Experiment 6

Slides were sequentially incubated
1. Primary antibody 80 seconds. (300 seconds for "Link" antibodies)
2. Goat-anti-Mouse F(ab')-HRP (D19150), 50 nM, 140 seconds
3. Conjugate D191851000 nM+5.8 mM DAB 80 seconds
4. Anti-FITC F(ab')-HRP (D19142), 150 nM, 140 seconds
5. 2.8 mM DAB 300 seconds.

The conjugate and DAB (step 3) were diluted in water solution of 50 mM imidazol-HCl pH 7.4, 56 mM hydrogen peroxide, 0.1% Tween. In step 5 DAB was diluted in 50 mM imidazol-HCl pH 7.4, 5.6 mM hydrogen peroxide, 0.1% Tween.

The procedure was carried out with 15 different antibodies on 12 different human tissues (as experiment 1).

The results of staining of high expression targets were similar to Envision Flex stains (regarding the intensity), but low expression targets were stained significantly more intense, and cellular structures not stained (+0) with Envision FLEX were moderately stained: anti-BCL-6 moderately stained a large proportion of nuclei in mamma carcinoma, in comparison, the stains of these areas with Envision FLEX were weak; the staining level with anti-estrogen receptor increased significantly in mamma carcinoma compared to Envision FLEX; anti-Carcinoembryonic Antigen staining of colon epithelial cells was more intense and robust than with Envision FLEX procedure; anti-synaptophysin weak to moderate staining were observed in all 12 tissues whereas very weak or no stais were observed with Envision FLEX. High expression structures were generally strongly stained, but not over stained, were sharp. Control slides without primary antibody had no staining at all.

The experiment shows that a combination of high (56 mM) concentration of hydrogen peroxide in the deposition solution and "normal" (5.6 mM) in the staining solution provide a powerful signal amplification system allowing a very fast sensitive and specific detection of antigens expressed in a broad dynamic range.

Experiment 7

Slides were sequentially incubated
1. Primary antibody 80 seconds. (300 seconds for "Link" antibodies)
2. Goat-anti-Mouse F(ab')-HRP (D19150), 20 nM, 80 seconds
3. Conjugate D19059 3.0 microM+2.8 mM DAB 200 seconds
4. Anti-DNP F(ab')-AP, 100 nM, 5 300 seconds
5. LPR Liquid Permanent Red (DAKO K3468) 300 seconds.

The solvents in all steps and washing buffer were as in experiment 1.

The procedure was carried out with 15 different antibodies on 12 different human tissues (as experiment 1).

The appearance of stains, while the red hue, was similar to Envision Flex stains with DAB. The hue ranged from intense pink (low expression targets) through rich red (medium expression targets) to burgundy red (high expression targets) and near-black red (very high expression targets) giving a good dynamic range. There was no background on control slides with out antibody in step 1.

The experiment shows that the amplification system of the present invention provides for a beneficial use of "less sensitive" chromogens like LPR for detection of antigens expressed in a broad dynamic range.

Experiment 8

Slides were sequentially incubated
1. Premixed Primary antibody and Goat-anti-Mouse F(ab')-HRP (D19150) diluted 1:1 in antibody S0809 (DAKO), 30 seconds.
2. Conjugate D19185 10 microM+DAB 280 micoM+56 mM $H_2O_2$, 30 seconds.

The solvent in step 2 was water solution of 50 mM imidazol-HCl pH 7.4, 5.6 mM hydrogen peroxide, 0.1% Tween.

The procedure was carried out with 15 different antibodies on 12 different human tissues (as experiment 1).

This protocol produced specific bright green fluorescent staining of the antigens, showing that mechanism of deposition of the conjugate according to the invention per se provides for a powerful and specific amplification of a signal associated with the target.

Experiment 9

Experiment 9 evaluates different conjugate molecules and binding agents of the invention.
Protocol:
All slides were subjected to the same protocol:
1. Anti-Cytokeratin (clone AE1/A3, Dako Catalog No. M3515) diluted 1:50 in S0809, 1 min;
2. Goat-anti-Mouse binding agents (Table 3) in ABCPT buffer*), 2 min;
3. Conjugate (Table 3) in 50 mM imidazol-HCL, pH 7.4, 58 mM hydrogen peroxide, 5.8 mM DAB, 1 min.
4. Anti-FITC-HRP binding agents (Table 3) in ABCPT buffer*), 2 min
5. 5.8 mM DAB in 50 mM imidazol-HCL, pH 7.4, 58 mM hydrogen peroxide, 1 min.
6. Counterstain with Haematoxilin, 5 min.
*) ABCPT buffer: 0.1% 4-aminoantipurine, 0.2% Procline 2% BSA, 0.2% Casein, 2% PEG, 0.1% Tween20, 0.1 M NaCL, 10 mM HEPES, pH 7.2

TABLE 3

| Slide ID | Goat anti mouse-HRP | Conjugate | Anti FITC-HRP conjugate |
| --- | --- | --- | --- |
| 1 | D19150 35 nM | D19185 1 µM | D19142 150 nM |
| 2 | D18175 35 nM | D19185 1 µM | D19142 150 nM |
| 3 | D18175 16 nM | D19185 1 µM | D19142 150 nM |
| 4 | D18175 8 nM | D19185 1 µM | D19142 150 nM |
| 5 | D18175 4 nM | D19185 1 µM | D19142 150 nM |
| 6 | D18175 2 nM | D19185 1 µM | D19142 150 nM |
| 7 | D19150 35 nM | D19185 1 µM | D18144 150 nM |
| 8 | D19150 35 nM | D19185 1 µM | D18144 80 nM |
| 9 | D19150 35 nM | D19185 1 µM | D18144 40 nM |
| 10 | D19150 35 nM | D19185 1 µM | D18144 20 nM |
| 11 | D19150 35 nM | D19185 1 µM | D18144 10 nM |
| 12 | D19150 35 nM | D17157 1 µM | D19142 150 nM |
| 13 | D19150 35 nM | D17157 2 µM | D19142 150 nM |
| 14 | D19150 35 nM | D17157 4 µM | D19142 150 nM |
| 15 | D19150 35 nM | D19037 1 µM | D19142 150 nM |
| 16 | D19150 35 nM | D19037 2 µM | D19142 150 nM |
| 17 | D19150 35 nM | D19037 4 µM | D19142 150 nM |
| 18 | D19150 35 nM | D19112 1 µM | D19142 150 nM |
| 19 | D19150 35 nM | D19112 2 µM | D19142 150 nM |
| 20 | D19150 35 nM | D19112 4 µM | D19142 150 nM |
| 21 | D19150 35 nM | D19185 1 µM | D19142 150 nM |
| 22 | D19150 35 nM | D19185 2 µM | D19142 150 nM |
| 23 | D19150 35 nM | D19185 4 µM | D19142 150 nM |
| 24 | D19150 35 nM | D18126 1 µM | D19142 150 nM |
| 25 | D19150 35 nM | D18126 2 µM | D19142 150 nM |
| 26 | D19150 35 nM | D18126 4 µM | D19142 150 nM |
| 27 | D19150 35 nM | D18090 14 nM | D19142 150 nM |
| 28 | D19150 35 nM | D18090 42 nM | D19142 150 nM |
| 29 | D19150 35 nM | D19185 1 µM | D19142 150 nM |

The protocol was tested on samples of 6 different tissues (liver, pancreas, mamma, tonsil, appendix and colon carcinoma) comprising both cytokeratin negative tissue, as well as low and high cytokeratin expression tissues.
Results:
Goat-Anti Mouse HRP Conjugates:
The $F(ab')_1$-$HRP_1$ conjugate D19150 (slide 1 and 29) was compared to an antibody-Dextran-HRP conjugate D18175 which has, on average, 1.4 antibodies and 10 HRP enzymes per conjugate (slides 2-6). Despite the much higher number of HRP enzymes in conjugate D 18175 the staining intensity of slide 2 was only marginally more intense than slides 1 and 29. Slide 3 was stained as intense as slides 1 and 27, decreasing the concentration of D18175, slides 4-6, led to progressively less intense stains. Unspecific background staining was present on slides 2-5 in samples of appendix smooth muscle tissue, but it was not observed on slides 1 and 29. Likewise, unspecific staining of folded tissue not present on slides 1 and 29 was observed on slides 2-6.

This indicates that abundance of HRP per binding agent that binds to a target does not add to amplification of the specific signal, but rather generates a noise signal.

Anti-FITC-HRP Conjugates:

The F(ab')$_1$-HRP$_1$ conjugate D19142 (slide 1 and 29) was compared to an antibody-Dextran-HRP conjugate D 18144 having on average 1.4 antibodies and 10 HRP enzymes/conjugate (slides 7-11). Despite the much higher number of HRP enzymes in conjugate D 18144 the staining intensity of slide 7 was only marginally more intense than slides 1 and 29. Slide 8 was stained as intense as slides 1 and 29, lowering the concentration of D18175 (slides 9-11) led to progressively less intense stains. On slides 7-11 a severe unspecific background staining, not observed on slides 1 and 29, was present in appendix smooth muscle tissue, and on slides 7-9 there was also background in tonsil germinal centers. Likewise, unspecific staining of folded tissue, not present on slides 1 and 29, was observed on slides 7-11.

This indicates that abundance of HRP per binding agent that binds to the deposited conjugate does not add to amplification of the specific signal, but rather generates a noise signal.

Conjugates:

6 different conjugates were compared:
D17157 (one ferulic acid, 1 fluorescein, slides 12-14);
D19037 (two ferulic acids, one fluorescein, slides 15-17);
D19112 (three ferulic acids, one fluorescein, slides 18-20);
D19185 (four ferulic acids, one fluorescein slides 1, 29 and 21-23);
D18126 (six ferulic acids, three fluoresceins, slides 24-26); and
D18090 (dextran conjugate with 101 ferulic acids and 72 fluoresceins).

The intensity of the stains increased progressively with the number of ferulic acid residues (Fer) per conjugate and clearly demonstrated the following trend: 1 Fer (D17157) <<2 Fer (D19037)<<3 Fer (D19112)<4 Fer (D19185). D19185 provided stains which were approximately as intense as with D19112 being doubled in concentration (compared to D19185), i.e. slides 19 and 21 and slides 20 and 22 were of similar intensity.

D18126 with 6 ferulic acids and three fluoresceins produced stains of similar intensity to D19185; however the stains with D18126 were much less crisp, which was particular noticeable in small-celled tissues such as the colon carcinoma. Another drawback of D18126 was that strongly stained areas, i.e. in tonsils, exhibited a halo of unspecific stain in neighbouring cells.

A very large dextran conjugate, D18090, showed a staining pattern that differed from the smaller conjugates of above. While samples with high expression of the targets demonstrated very intense staining (+3-+4) (e.g. slide 28 was similar to slide 1 and 29 in this regard), samples with low expression of the targets (e.g. in pancreas and especially liver) were hardly stained at all (+0-+0.5).

Experiment 10

Experiment 10 demonstrates the influence of concentrations of DAB and $H_2O_2$ in the conjugate deposition media.

Protocol:

All slides were subjected to the same protocol:
1. Anti-Cytokeratin (clone AE1/A3, Dako Catalog No. M3515) diluted 1:200 in S0809, min
2. Goat-anti-mouse (D19150) in ABCPT buffer, 2 min
3. 1 microM conjugate D19185 in 50 mM imidazol-HCL, pH 7.4, with varying DAB and $H_2O_2$ (Table 4), 1 min or 3 min.
4. 150 nM antiFITC-HRP (D19142) in ABCPT buffer, 2 min.
5. 5.5 mM DAB in 50 mM imidazol-HCL, pH 7.4, 58 mM hydrogen peroxide, 1 min.
6. Counterstain with Haematoxilin, 5 min.

TABLE 4

| Slide | DAB (mM) | $H_2O_2$ (mM) | Time (min) |
| --- | --- | --- | --- |
| 1 | 5.5 | 147 | 1 |
| 2 | 5.5 | 58 | 1 |
| 3 | 5.5 | 15 | 1 |
| 4 | 5.5 | 5.8 | 1 |
| 5 | 5.5 | 1.5 | 1 |
| 6 | 5.5 | 147 | 3 |
| 7 | 5.5 | 58 | 3 |
| 8 | 5.5 | 15 | 3 |
| 9 | 5.5 | 5.8 | 3 |
| 10 | 5.5 | 1.5 | 3 |
| 11 | 2.8 | 147 | 1 |
| 12 | 2.8 | 58 | 1 |
| 13 | 2.8 | 15 | 1 |
| 14 | 2.8 | 5.8 | 1 |
| 15 | 2.8 | 1.5 | 1 |
| 16 | 2.8 | 147 | 3 |
| 17 | 2.8 | 58 | 3 |
| 18 | 2.8 | 15 | 3 |
| 19 | 2.8 | 5.8 | 3 |
| 20 | 2.8 | 1.5 | 3 |
| 21 | 1.4 | 147 | 1 |
| 22 | 1.4 | 58 | 1 |
| 23 | 1.4 | 15 | 1 |
| 24 | 1.4 | 5.8 | 1 |
| 25 | 1.4 | 1.5 | 1 |
| 26 | 1.4 | 147 | 3 |
| 27 | 1.4 | 58 | 3 |
| 28 | 1.4 | 15 | 3 |
| 29 | 1.4 | 5.8 | 3 |
| 30 | 1.4 | 1.5 | 3 |

The protocols were tested on 6 different tissues (liver, pancreas, mamma, tonsil, appendix and colon carcinoma) comprising both cytokeratin negative tissue, as well as low and high expression targets.

Results:

Intensity of staining: With regard to intensity of the stains, there was observed a clear trend that a higher DAB concentration in the conjugate deposition solution leads to less intense stains, i.e. 5.5 mM DAB<2.8 mM DAB<1.4 mM DAB. The increased intensity, however, also correlated with decreased crispness of the staining. This was especially visible in the small-celled structures of the colon carcinoma. Across all tissues the counterstained blue nuclei stood out more distinct and clear in slides treated with a higher DAB concentration, than with a lower concentration.

15 mM hydrogen peroxide in the conjugate deposition solution was optimal to produce most intense stainings, however it was a broad optimum with a small difference between 5.8, 15 and 58 mM. An increase to 147 mM $H_2O_2$ in the solution in all cases led to a significantly less intense staining. At 1.5 mM hydrogen peroxide the stains were also less intense, if the incubation time was 1 min, however in this case the intensity could be slightly increased by increasing the incubation time to 3 min.

The intensity of staining was dependent on duration of incubation time when concentrations of DAB and hydrogen peroxide concentration were lowered, and it was independent of the incubation time when the concentrations were high. Slides incubated in the presence of high DAB and high $H_2O_2$ (slides 1-3 (1 min) and slides 6-8 (3 min)) looked identical, as well as slides 11 and 12 looked identical to slides 16 and 17 correspondingly. At the other side, slides 28-30 (low DAB, low $H_2O_2$, 3 min) were significantly more intensively stained than slides 23-25 (low DAB, low $H_2O_2$, 1 min). This enhancement with increasing time was most pronounced for low expression targets in liver and pancreas.

Conclusions:

The experiments 10 and 11 demonstrate that a broad range of binding agents, conjugates and reaction conditions can be used. What is "optimal" depends on the intended application, however to obtain a fast and crisp IHC staining having a typical pattern, i.e. resembling a typical staining produced by the Envision Flex system, (DAKO, K8010) the following combinations may be recommended:

(1) Smaller $F(ab')_1$-$HRP_1$ conjugates provides better signal to noise than larger dextran conjugates both when it comes to recognition of the primary antibody in step 2 (D19150), as well as to recognition of the conjugates in step 4 (D19142).

(2) The conjugates having within their molecules a first area comprising two to four peroxidase substrates which are closely spaced within this area, i.e. a distance between two neighboring peroxidase substrates is less than 2.5 nm, e.g. equal to the size of two juxtaposed lysines, and a second area comprising a single detectable moiety, wherein these two areas are separated within said conjugate molecules by a distance of more than 2.5. nm, e.g. 3-20 nm, are most efficient conjugates of the invention, i.e. they are deposited precisely around target sites, i.e. any unspecific deposition leading to consequent background staining and/or reduced crispness is avoided. An example of such conjugates may be D19185 comprising 4 ferulic acid residues, 1 fluorescein separated by L150 linker (structure of D19185 is shown in FIG. 1(3)).

(3) Using the low background binding agents D19150 and D19142 in combination with the efficient conjugates D19112 and D19185 may provide for very fast and background-free specific signal amplification over a wide range of conditions.

(4) IHC stains that supersede any traditional IHC stain (on all accounts) can be prepared by deliberately sacrificing the abundant signal intensity in favor of an increased crispness by using high hydrogen peroxide and high DAB in step 3, i.e. the method provides for a shorter protocol time, less amount of binding agents, broader dynamic range of target detection, better signal to noise, higher signal intensity both high and very low expression targets, and increased crispness of staining.

(5) For some special applications, other conjugates or incubation conditions (than as of (1) to (3) above) can be used. It can be illustrated by experiment 10, slide 27 and 28 that were stained using the large dextran conjugate D18090: these slides were tissues with high expression targets and they were over-stained (+4). This could be used if a yes/no result is desired or in case if it is desired to suppress a weak background, i.e. from the primary antibody. Conversely, as illustrated by experiment 11 slides 28-30, low DAB (1.4. mM), low hydrogen peroxide (5.8 mM and 15. mM) (in combination with an extended reaction time in case of 1.5. mM hydrogen peroxide, slide 30) may be advantageously used to enhance staining of low expression targets without over staining high expression targets.

Experiment 12

It has been reported (Volante M. et al (2000) J Histochem Cytochem 48:1583-1585) that post-incubation heating significantly improves tyramide signal amplification (described in U.S. Pat. Nos. 5,863,748; 5,688,966; 5,767,287; 5,731, 158; 5,583,001, 5,196,306, 6,372,937 or 6,593,100 (discussed above) and by Bobrow M N, et al (1989) J Immunol Methods 125:279-285; and Bobrow M N, et al (1992) J Immunol Methods 150:45-49). Experiment 12 evaluates of the conditions of post-deposition heating on the results of staining with Liquid Permanent Red (LPR) according to the method of the present method.

12 slides were treated with three different antibodies of the Table (see Experiment 1):
  1. Mouse Anti-Cytokeratin (dilution 1:50)
  2. Mouse Anti-CD20 (dilution 1:200)
  3. Mouse Anti-BCL6 (dilution 1:75)
according to protocol A or B below.

Protocol A
1. Primary antibody, 1 min[1, 2] or 5 min[3],
2. Goat-anti-Mouse F(ab')-HRP (D19150), 40 nM in ABCPT buffer, 1 min;
3. Wash in S3006 (DAKO) at room temperature 2 min
4. Deposition media: Conjugate D21030 100 nM+0.8 mM DAB+5.8 mM $H_2O_2$, 1 min
5. Wash in S3006 at room temperature 2 min, or boiling in microwave oven, 5 min
6. Anti-FITC F(ab')-AP, 100 nM in ABCPT buffer, 3 min
7. Wash in S3006 at room temperature 2 min
8. LPR, 5 min.

Protocol B
1. Primary antibody, 1 min[1, 2] or 5 min[3],
2. Goat-anti-Mouse F(ab')-HRP (D19150), 40 nM in ABCPT buffer, 1 min;
3. Wash in S3006 (DAKO) at room temperature 5 min
4. Conjugate D21030 1 μM+2.8 mM DAB+5.8 mM $H_2O_2$, 1 min
5. Wash in S3006 at room temperature 5 min, or boiling in microwave oven, 5 min
6. Anti-FITC F(ab')-AP, 100 nM in ABCPT buffer, 3 min
7. Wash in S3006 at room temperature 5 min
8. LPR, 5 min.

Results

All 12 slides run with 3 different antibodies were stained ranging from +0.5 to +3). Evaluation of the results of "high" versus "low" DAB protocol, and "high temperature" versus "low temperature" protocol results for CD20, a high expression marker, revealed a noticeable, but little difference in intensity of staining in the presence of high DAB (+2.5) or low DAB (+3) and washing at room temperature, or high DAB & high temperature (+2) versus low DAB& high temperature (+1.5). The same but much more significant difference (high DAB+2, low DAB+3; room temperature wash) was observed for cytokeratin in samples where the target is low expressed (in particular, in liver and kidney samples). The effect of boiling wash was seen even more clearly than the effect of DAB concentration, as it caused a distinctive drop in staining intensity of these tissues with low expression of cytokeratin (from +1.5 (low DAB) to +0.5 (high DAB)).

With BCL6 there was little difference between high and low protocols, but again slide receiving boiling wash were noticeably less intense than those that were washed at room temperature.

The experiment shows that boiling wash after the precipitation step causes a decrease in staining intensity, clearly visible in case of sensitive low expression targets. These findings are in contrast to the findings by Volante M. et al (2000) (above ref.), where a dramatic increase in staining intensity has been reported as a consequence of boiling wash following the conjugate, i.e. biotynil-tyramide, deposition step.

Without to be bound to a theory, we speculate that conjugate deposition described herein is primarily associated with formation of water insoluble precipitates comprising the conjugate molecules of the present invention (covalently bound to each other) and/or precipitates comprising DAB and the conjugate molecules Such precipitates can be partially washed away when the sample is subjected boiling after precipitation procedure because the precipitates do not form firm covalent bonds with target proteins of the sample. In contrast, biotinyl-tyramide conjugate molecules are deposited on aromatic amino acids, where they form covalent bonds. The aromatic amino acids are typically hidden within protein structure. Post-incubation heating causing protein denaturation may facilitate exposure aromatic residues bound to tyramide and increase thereby the specific signal, while removing non-specific biotinyl-tyramide precipitates.

The invention claimed is:
1. A water soluble conjugate that comprises:
   (i) one or more labels;
   (ii) two to four moieties of peroxidase substrate, each of which is capable of serving as substrate of an enzyme with peroxidase activity and each is a residue of the following formula:

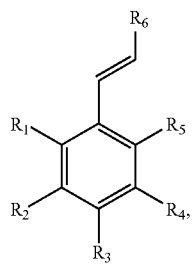

wherein
R1 is —H, —O—X, —N(X)$_2$ or —S—X;
R2 is —H, —O—X, —N(X)$_2$, or —S—X;
R3 is —H, —OH, —NH$_2$ or —SH;
R4 is —H, —O—X, —N(X)$_2$, or —S—X;
R5 is —H, —O—X, —N(X)$_2$, or —S—X;
R6 is —CO—N(X)$_2$, or —CO—X; and
wherein
H is hydrogen;
O is oxygen;
S is sulphur;
N is nitrogen; and
X is H, alkyl, or aryl;
wherein the labels (i) and moieties of peroxidase substrate (ii) are not the same chemical substances;
wherein the labels (i) and moieties of peroxidase substrate (ii) are linked together via a linker, wherein said linker is a compound consisting of a linear chain of at least 30 consecutively connected atoms and two branching points, the first branching point at one end of the linear chain connecting the linear chain to the first of the one or more labels, and the second branching point at the other end of the linear chain connecting the linear chain to the first moiety of the two to four moieties of peroxidase substrate;
wherein each of the moieties of peroxidase substrate JO is connected to the linker group via R6;
wherein the first label of the one or more labels (i) is separated from the moieties of peroxidase substrate (ii) by the linker; and
wherein the moieties are consecutively connected to each other by spacers such that any two moieties of peroxidase substrate are separated from each other by 5 to 30 consecutively connected atoms.

2. The conjugate according to claim 1, wherein the moieties of peroxidase substrate are residues of ferulic acid, cinnamic acid, amino cinnamic acid, caffeic acid, or sinapinic acid.

3. The conjugate according to claim 1, wherein at least two of the moieties of peroxidase substrate are tyrosine residues.

4. The conjugate according to claim 1, wherein the linear chain is a polymer that comprises 2 to 10 repeats of the following formula:

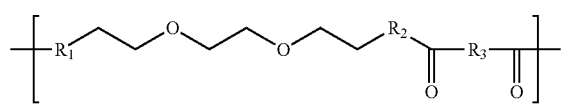

wherein R$_1$ and R$_2$ are selected from NH and O, and R$_3$ is selected from methyl, ethyl, propyl, CH$_2$OCH$_2$ and (CH$_2$OCH$_2$)$_2$, and wherein each of the 2 to 10 repeats contains no more than three consecutively repeating ethyloxy groups.

5. The conjugate of claim 4, wherein the conjugate comprises one label.

6. The conjugate of claim 4, wherein the label is a fluorescent substance or a member of a specific binding pair.

7. The conjugate of claim 4, wherein at least one moiety with peroxidase activity is Horseradish peroxidase.

8. The conjugate of claim 4, wherein the conjugate comprises one fluorescein label and four moieties of ferulic acid, and the linear chain comprises 2 to 10 repeats of the formula

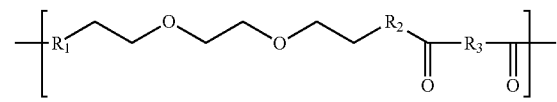

9. The conjugate according to claim 1, wherein the conjugate comprises one label.

10. The conjugate according to claim 1, wherein the linker comprises a dextran polymer and at least one first and at least one second linear polymers, wherein said at least one first polymer is conjugated to two to four moieties of peroxidase substrate and wherein at least one said second polymer is conjugated to one or more labels, and wherein said at least one first and at least one second polymers are conjugated to the dextran.

11. The conjugate according to claim 10, wherein the at least one second polymer comprises two or more labels, wherein the molecular distance between each of said two or more labels is at least 30 consecutively connected atoms.

12. The conjugate according to claim 1, wherein the label is a fluorescent substance or a member of a specific binding pair.

13. The conjugate according to claim 1, wherein the enzyme with peroxidase activity is Horseradish peroxidase.

14. A composition comprising a conjugate according to claim 1.

15. A kit-of-parts for detection of a target comprising peroxidase activity in a sample, wherein the kit-of-parts comprises the conjugate of claim 1.

16. A method for detection of a target comprising peroxidase activity in a sample, the method comprising:
   I. incubating a sample supposedly comprising a target comprising peroxidase activity in a water solution, wherein the water solution comprises:
      a) a conjugate according to claim 1;
      b) 3,3' diaminobenzidine; and
      c) a peroxide compound, thereby forming a precipitate of the conjugate;
   II. detecting the precipitate of the compound in the sample, thereby detecting peroxidase activity in the sample.

17. The method according to claim 16, wherein the water solution of (I) comprises more than 5 mM hydrogen peroxide and between 0.25 mM and 6 mM 3,3' diaminobenzidine.

18. The method according to claim 16, wherein the amount of 3,3' diaminobenzidine is above 1.5 mM.

19. The method according to claim 16, wherein the peroxidase activity is associated with Horseradish peroxidase.

20. The method according to claim 19, wherein Horseradish peroxidase is the target or is directly or indirectly linked to the target.

21. The method according to claim 20, wherein the target is a polypeptide, nucleic acid, carbohydrate, lipid or a derivative thereof, molecular complex, particle, eukaryotic or prokaryotic cell or microorganism.

22. The method according to claim 16, wherein the sample is a biological sample, environmental sample, or chemical sample.

23. The method according to claim 22, wherein the sample is immobilized onto a solid support.

24. A water soluble conjugate comprising the formula:

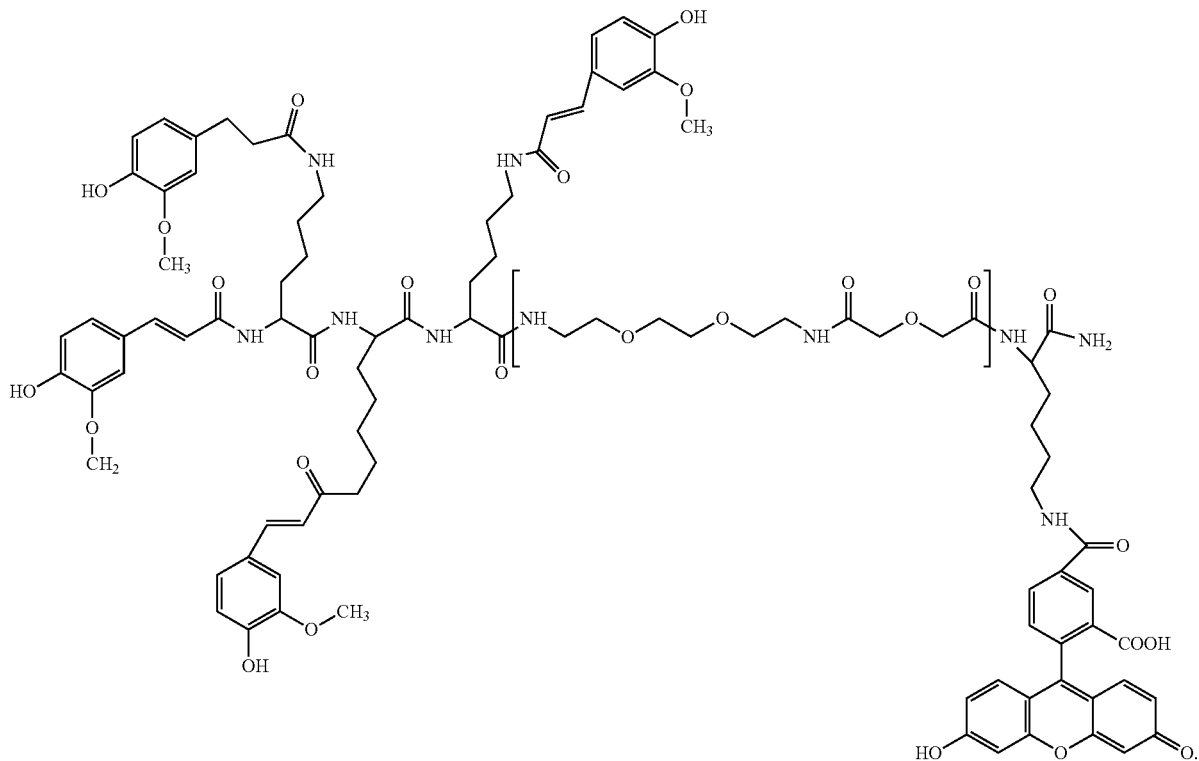

* * * * *

UNITED STATES PATENT AND TRADEMARK OFFICE
CERTIFICATE OF CORRECTION

| | | |
|---|---|---|
| PATENT NO. | : 9,671,400 B2 | |
| APPLICATION NO. | : 12/708702 | |
| DATED | : June 6, 2017 | |
| INVENTOR(S) | : Jesper Lohse | |

It is certified that error appears in the above-identified patent and that said Letters Patent is hereby corrected as shown below:

On the Title Page

In item (56), in Column 2, under "Other Publications", Line 8, delete "Specificty"," and insert -- Specificity", --, therefor.

In the Specification

In Column 1, Line 14, delete "peorxidase" and insert -- peroxidase --, therefor.

In Column 2, Lines 41-42, delete "immunohystochemistry" and insert -- immunohistochemistry --, therefor.

In Column 5, Line 25, delete "suppot" and insert -- support. --, therefor.

In Column 5, Line 32, delete "mM" and insert -- mM. --, therefor.

In Column 5, Line 35, delete "reporeter" and insert -- reporter --, therefor.

In Column 5, Line 59, delete "heretoatoms," and insert -- heteroatoms, --, therefor.

In Column 6, Lines 4-5, delete "3,3'-diaminobenzedine" and insert -- 3,3'-diaminobenzidine --, therefor.

In Column 6, Line 9, delete "3,3'-diaminobenzedine" and insert -- 3,3'-diaminobenzidine --, therefor.

In Column 6, Lines 12-13, delete "3,3'-diaminobenzedine" and insert -- 3,3'-diaminobenzidine --, therefor.

Signed and Sealed this
Third Day of October, 2017

Joseph Matal
*Performing the Functions and Duties of the*
*Under Secretary of Commerce for Intellectual Property and*
*Director of the United States Patent and Trademark Office*

CERTIFICATE OF CORRECTION (continued)  Page 2 of 4
U.S. Pat. No. 9,671,400 B2

In Column 6, Lines 20-21, delete "interchangebly" and insert -- interchangeably --, therefor.

In Column 6, Line 23, delete "ezyme" and insert -- enzyme --, therefor.

In Column 7, Line 48, delete "sinapinicacid" and insert -- sinapinic acid --, therefor.

In Column 8, Line 61, delete "3,3'-diaminobenzedine" and insert -- 3,3'-diaminobenzidine --, therefor.

In Column 8, Lines 64-65, delete "environment" and insert -- environment. --, therefor.

In Column 9, Line 30, delete "digoxiginin," and insert -- digoxigenin, --, therefor.

In Column 9, Line 36, delete "zink" and insert -- zinc --, therefor.

In Column 10, Line 65, delete "cellolosics" and insert -- cellulosics --, therefor.

In Column 11, Line 29, delete "dextran" and insert -- dextran. --, therefor.

In Column 12, Line 20, delete "hexan di isocyanate," and insert -- hexane diisocyanate, --, therefor.

In Column 12, Line 24, delete "cabodiimide." and insert -- carbodiimide. --, therefor.

In Column 12, Line 66, delete "peorxidase" and insert -- peroxidase --, therefor.

In Column 17, Line 35, delete "strepavidin" and insert -- streptavidin --, therefor.

In Column 22, Line 34, delete "proxidase" and insert -- peroxidase --, therefor.

In Column 24, Lines 32-33, delete "pyrolidone" and insert -- pyrrolidone --, therefor.

In Column 25, Line 48, delete "agent" and insert -- agent. --, therefor.

In Column 25, Line 56, delete "pyrolidone" and insert -- pyrrolidone --, therefor.

In Column 26, Line 27, delete "azid," and insert -- azide, --, therefor.

In Column 29, Line 12, delete "immunohytochemistry" and insert -- immunohistochemistry --, therefor.

In Column 29, Line 14, delete "biolodical" and insert -- biological --, therefor.

In Column 29, Line 19, delete "ICH" and insert -- IHC --, therefor.

In Column 30, Line 25, delete "benzoequinone," and insert -- benzoquinone, --, therefor.

In Column 30, Line 51, delete "glycin-HCl" and insert -- glycine-HCl --, therefor.

In Column 32, Line 62, delete "Pyrolidon" and insert -- Pyrrolidone --, therefor.

In Column 34, Line 2, delete "guanuine-9-acetic acid," and insert -- guanine-9-acetic acid, --, therefor.

In Column 34, Line 3, delete "6-thuioguanine-9-acetic acid," and insert -- 6-thioguanine-9-acetic acid, --, therefor.

In Column 36, Line 53, delete "tyrosin" and insert -- tyrosine --, therefor.

In Column 36, Line 59, delete "grpoup" and insert -- group --, therefor.

In Column 37, Lines 10-11, delete "2,4-dinitro-fluor-benzene" and insert -- 2,4-dinitro-fluorobenzene --, therefor.

In Column 37, Line 50, delete "aminogroups" and insert -- amino groups --, therefor.

In Column 38, Line 24, delete "proprioninc" and insert -- propionic --, therefor.

In Column 38, Line 40, delete "fluorescin" and insert -- fluorescein --, therefor.

In Column 39, Line 10, delete "sinnapinic" and insert -- sinapinic --, therefor.

In Column 39, Line 47, delete "fluoresceine," and insert -- fluorescein, --, therefor.

In Column 39, Line 67, delete "HPLC:" and insert -- HPLC. --, therefor.

In Column 41, Lines 10-11, delete "sinapinnic" and insert -- sinapinic --, therefor.

In Column 42, Line 12, delete "N-termina" and insert -- N-terminal --, therefor.

In Column 42, Lines 33-34, delete "fluorescien" and insert -- fluorescein --, therefor.

In Column 43, Line 20, delete "4054" and insert -- 4054. --, therefor.

In Column 43, Line 23, delete "3447" and insert -- 3447. --, therefor.

In Column 44, Line 29, delete "micoL" and insert -- microL --, therefor.

In Column 44, Line 61, delete "ration" and insert -- ratio --, therefor.
In Column 45, Line 27, delete "1))" and insert -- 1) --, therefor.

In Column 45, Line 41, delete "ProstataSpesificAntigem," and insert -- Prostate Specific Antigen, --, therefor.

In Column 45, Line 61, delete "perfomed" and insert -- performed --, therefor.

In Column 46, Line 15, delete "Tween-20" and insert -- Tween-20. --, therefor.

In Column 48, Line 25, delete "1-4)" and insert -- 1-4). --, therefor.

In Column 49, Line 5, delete "moderatly" and insert -- moderately --, therefor.

In Column 49, Line 15, delete "stais" and insert -- stains --, therefor.

In Column 49, Line 47, delete "with out" and insert -- without --, therefor.

In Column 54, Line 64, delete "biotynil-tyramide," and insert -- biotinyl-tyramide, --, therefor.

In the Claims

In Column 55, Line 43, in Claim 1, delete "—CO—N(X)$_2$, or —CO—X;" and insert -- —CO—N(X)$_2$; --, therefor.

In Column 55, Line 61, in Claim 1, delete "JO" and insert -- (ii) --, therefor.

In Column 56, Line 40, in Claim 8, after "  " insert -- . --.